United States Patent [19]
Dalrymple et al.

[11] Patent Number: 5,298,423
[45] Date of Patent: Mar. 29, 1994

[54] NUCLEOTIDE SEQUENCES ENCODING THE EXPRESSION OF A HANTAAN VIRUS NUCLEOCAPSID PROTEIN AND G1 AND G2 GLYCOPROTEINS

[75] Inventors: Joel M. Dalrymple, Myersville; Connie S. Schmaljohn, Frederick, both of Md.

[73] Assignee: The United States of America as represented by the Secretary of the Army, Washington, D.C.

[21] Appl. No.: 799,479

[22] Filed: Nov. 14, 1991

Related U.S. Application Data

[63] Continuation of Ser. No. 125,105, Nov. 25, 1987, abandoned.

[51] Int. Cl.$^5$ .................. C12N 15/00; C12N 15/33
[52] U.S. Cl. .................. 435/320.1; 536/23.72
[58] Field of Search .......... 536/27, 23.72; 435/91, 435/172.3, 320.1, 948, 236, 69.1, 320.1; 935/6, 23, 60

[56] References Cited

PUBLICATIONS

Schmaljohn et al. 1986 *Virology* 155: 633–643.
Schmaljohn et al., 1987 *Virology* 157: 31–39.
Yoo et al., 1987 *NAR* 15:6299–6300.

*Primary Examiner*—Richard A. Schwartz
*Assistant Examiner*—Gary L. Brown
*Attorney, Agent, or Firm*—Werten F. W. Bellamy; John Francis Moran

[57] ABSTRACT

Nucleotide sequences coding for Hantaan virus nucleocapsid protein and glycoproteins G1 and G2 can be used to produce these proteins for vaccine and diagnostic applications.

13 Claims, 8 Drawing Sheets

FIG. 2A

```
    1
TAGTAGTAGACTCCCTAAAGAGCTACTAGAACAACG MET ALA THR MET GLU GLU LEU GLN ARG GLU ILE
                                     ATG GCA ACT ATG GAG GAA TTA CAG AGG GAA ATC

70
ASN ALA HIS GLU GLY GLN LEU VAL ILE ALA ARG GLN LYS VAL ARG ASP ALA GLU LYS GLN
AAT GCC CAT GAG GGT CAA TTA GTG ATA GCC AGG CAG AAG GTG AGG GAT GCA GAA AAA CAG

130
TYR GLU LYS ASP PRO ASP GLU LEU ASN LYS ARG THR LEU THR ASP ARG GLU GLY VAL ALA
TAT GAA AAG GAT CCA GAT GAG TTG AAC AAG AGA ACA TTA ACT GAC CGA GAG GGC GTT GCA

190
VAL SER ILE GLN ALA LYS ILE ASP GLU LEU LYS ARG GLN LEU ALA ASP ARG ILE ALA THR
GTA TCT ATC CAG GCA AAA ATT GAT GAG TTA AAA AGG CAA CTG GCA GAT AGG ATT GCA ACT

250
GLY LYS ASN LEU GLY LYS GLU GLN ASP PRO THR GLY VAL GLU PRO GLY ASP HIS LEU LYS
GGG AAA AAC CTT GGG AAG GAA CAA GAT CCA ACA GGG GTG GAG CCT GGA GAC CAT CTG AAA

310
GLU ARG SER MET LEU SER TYR GLY ASN VAL LEU ASP LEU ASN HIS LEU ASP ILE ASP GLU
GAG AGG TCA ATG CTC AGT TAT GGT AAT GTG CTG GAT TTA AAC CAT TTG GAT ATT GAT GAA

370
PRO THR GLY GLN THR ALA ASP TRP LEU SER ILE ILE VAL TYR LEU THR SER PHE VAL VAL
CCT ACA GGA CAG ACA GCA GAC TGG CTG AGC ACT ACT GTC TAT CTT ACA TCC TTT GTC GTC

430
PRO ILE LEU LEU LYS ALA LEU TYR MET LEU THR THR ARG GLY ARG GLN THR THR LYS ASP
CCG ATA CTT CTG AAA GCT CTG TAT ATG TTG ACA ACA AGG GGG AGG CAA ACT ACC AAG GAT

490
ASN LYS GLY THR ARG ILE ARG PHE LYS ASP ASP SER SER PHE GLU ASP VAL ASN GLY ILE
AAT AAA GGG ACC CGG ATT CGA TTT AAG GAT GAT AGC TCG TTC GAG GAT GTT AAC GGT ATC

550
ARG LYS PRO LYS HIS LEU TYR VAL SER LEU PRO ASN ALA GLN SER SER MET LYS ALA GLU
CGG AAA CCA AAA CAT CTT TAC GTG TCC TTG CCA AAT GCA CAG TCA AGC ATG AAG GCA GAA

610
GLU ILE THR PRO GLY ARG TYR ARG THR ALA VAL CYS GLY LEU TYR PRO ALA GLN ILE LYS
GAG ATT ACA CTT GGT AGA TAT AGA ACA GCA GTC TGT GGG CTC TAC CCT GCA CAG ATT AAG

670
ALA ARG GLN MET ILE SER PRO VAL MET SER VAL ILE GLY PHE LEU ALA LEU ALA LYS ASP
GCA CGG CAG ATG ATC AGT CCA GTT ATG AGT GTA ATT GTT TTT CTA GCA TTA GCA AAG GAC

730
TRP SER ASP ARG ILE GLU GLN TRP LEU ILE GLU PRO CYS LYS LEU LEU PRO ASP THR ALA
TGG ATG GAT CGT ATC GAA CAA TGG TTA ATT GAA CCT TGC AAG CTT CTT CCA GAT ACA GCA
```

FIG. 2B

790
ALA VAL SER LEU LEU GLY GLY PRO ALA THR ASN ARG ASP TYR LEU ARG GLN ARG GLN VAL
GCA GTT AGC CTC CTT GGT GGT CCT GCA ACA AAC AGG GAC TAC TTA CGG CAG CGG CAA GTG

850
ALA LEU GLY ASN MET GLU THR LYS GLU SER LYS ALA ILE ARG GLN HIS ALA GLU ALA ALA
GCA TTA GGC AAT ATG GAG ACA AAG GAG TCA AAG GCT ATA CGC CAG CAT GCA GAA GCA GCT

910
GLY CYS SER MET ILE GLU ASP ILE GLU SER PRO SER SER ILE TRP VAL PHE ALA GLY ALA
GGC TGT AGC ATG ATT GAA GAT ATT GAG TCA CCA TCA TCA ATA TGG GTT TTT GCT GGA GCA

970
PRO ASP ARG CYS PRO PRO THR CYS LEU PHE ILE ALA GLY ILE ALA GLU LEU GLY ALA PHE
CCA GAC CGT TGT CCA CCA ACA TGT TTG TTT ATA GCA GGT ATT GCT GAG CTT GGG GCA TTT

1030
PHE SER ILE LEU GLN ASP MET ARG ASN THR ILE MET ALA SER LYS THR VAL GLY THR SER
TTT TCC ATC CTG CAG GAC ATG CGA AAT ACA ATC ATG GCA TCT AAG ACA GTT GGA ACA TCT

1090
GLU GLU LYS LEU ARG LYS LYS SER SER PHE TYR GLN SER TYR LEU ARG ARG THR GLN SER
GAG GAG AAG CTA CGG AAG AAA TCA TCA TTT TAT CAG TCC TAC CTC AGA AGG ACA CAA TCA

1150
MET GLY ILE GLN LEU GLY GLN ARG ILE ILE VAL LEU PHE MET VAL ALA TRP GLY LYS GLU
ATG GGG ATA CAA CTA GGC CAG AGA ATT ATT GTG CTC TTC ATG GTT GCC TGG GGA AAG GAG

1210
ALA VAL ASP ASN PHE HIS LEU GLY ASP ASP MET ASP PRO GLU LEU ARG THR LEU ALA GLN
GCT GTG GAC AAC TTC CAC TTA GGG GAT GAT ATG GAT CCT GAG CTA AGG ACA CTG GCA CAG

1270
SER LEU ILE ASP VAL LYS VAL LYS GLU ILE SER ASN GLN GLU PRO LEU LYS LEU *** TTA
AGC TTG ATT GAT GTC AAA GTG AAG GAA ATC TTC AAC CAA GAG CCT TTG AAA CTC TAA

1330
ATGAATGTATTAATCCTTTTATGTGATTATCATATACTACTGAATCATTATCAATCATATTTGCACTATTATTATCAGGG

1410
GAATCAGTATATCAGGGCATGGGAACATTTATGGGTGGGAATCATTACTCAGGGGTGGGTCAGTTAATCCGTTGTGGGTG

1490
GGTTTAGCTCCAGGCTACCTTAAGTAGCCTTTTTTTGTATATATGGATGTAGATTTCATTTGATCCTTAACTAATCTTGT

1570
TTTCTTTCCCTTTCTTTCTGCTTTCTCTGCTTACTAACAACAACATTCTACCTCAACACAAAACTACCTCAACTTAACTA

1650
CCTCATTTGATTGCTCCTGATTGTCTTTTTAGGGAGCATACTACTA

FIG. 3A

```
                                        10        20        30        40
                              TAGTAGTAGACACCGCAAAAGAAAGCAGTCAATCAGCAAC

41                                                      G₁ >
     MET GLY ILE TRP LYS TRP LEU VAL MET ALA SER LEU VAL TRP PRO VAL LEU THR LEU ARG
     ATG GGG ATA TGG AAG TGG CTA GTG ATG GCC AGT TTA GTA TGG CCT GTT TTG ACA CTG AGA

101
     ASN VAL TYR ASP MET LYS ILE GLU CYS PRO HIS THR VAL SER PHE GLY GLU ASN SER VAL
     AAT GTC TAT GAC ATG AAA ATT GAG TGC CCC CAT ACA GTA AGT TTT GGG GAA AAC AGT GTG

161
     ILE GLY TYR VAL GLU LEU PRO PRO VAL PRO LEU ALA ASP THR ALA GLN MET VAL PRO GLU
     ATA GGT TAT GTA GAA TTA CCC CCC GTG CCA TTG GCC GAC ACA GCA CAG ATG GTG CCT GAG

221
     SER SER CYS ASN MET ASP ASN HIS GLN SER LEU ASN THR ILE THR LYS TYR THR GLN VAL
     AGT TCT TGT AAC ATG GAT AAT CAC CAA TCG TTG AAT ACA ATA ACA AAA TAT ACC CAA GTA

281
     SER TRP ARG GLY LYS ALA ASP GLN SER GLN SER SER GLN ASN SER PHE GLU THR VAL SER
     AGT TGG AGA GGA AAG GCT GAT CAG TCA CAG TCT AGT CAA AAT TCA TTT GAG ACA GTG TCC

341
     THR GLU VAL ASP LEU LYS GLY THR CYS VAL LEU LYS HIS LYS MET VAL GLU GLU SER TYR
     ACT GAA GTT GAC TTG AAA GGA ACA TGT GTT CTA AAA CAC AAA ATG GTG GAA GAA TCA TAC

401                                    *
     ARG SER ARG LYS SER VAL THR CYS TYR (ASP LEU SER) CYS ASN SER THR TYR CYS LYS PRO
     CGT AGT AGG AAA TCA GTA ACC TGT TAC (GAC CTG TCT) TGC AAT AGC ACT TAC TGC AAG CCA

461
     THR LEU TYR MET ILE VAL PRO ILE HIS ALA CYS ASN MET MET LYS SER CYS LEU ILE ALA
     ACA CTA TAC ATG ATT GTA CCA ATT CAT GCA TGC AAT ATG ATG AAA AGC TGT TTG ATT GCA

521
     LEU GLY PRO TYR ARG VAL GLN VAL VAL TYR GLU ARG SER TYR CYS MET THR GLY VAL LEU
     TTG GGA CCA TAC AGA GTA CAG GTG GTT TAT GAG AGA AGT TAC TGT ATG ACA GGA GTC CTG

581
     ILE GLU GLY LYS CYS PHE VAL PRO ASP GLN SER VAL VAL SER ILE ILE LYS HIS GLY ILE
     ATT GAA GGG AAA TGC TTT GTC CCA GAT CAA AGT GTG GTC AGT ATT ATC AGG CAT GGG ATC

641
     PHE ASP ILE ALA SER VAL HIS ILE VAL CYS PHE PHE VAL ALA VAL LYS GLY ASN THR TYR
     TTT GAT ATT GCA AGT GTT CAT ATT GTA TGT TTC TTT GTT GCA GTT AAA GGG AAT ACT TAT

701                                                *
     LYS ILE PHE GLU GLN VAL LYS LYS SER PHE GLU SER THR CYC (ASN ASP THR) GLU ASN LYS
     AAA ATT TTT GAA CAG GTT AAG AAA TCC TTT GAA TCA ACA TGC (AAT GAT ACA) GAG AAT AAA

761
     VAL GLN GLY TYR TYR ILE CYS ILE VAL GLY GLY ASN SER ALA PRO ILE TYR VAL PRO THR
     GTG CAA GGA TAT TAT ATT TGT ATT GTA GGG GGA AAC TCT GCA CCA ATA TAT GTT CCA ACA

821
     LEU ASP ASP PHE ARG SER MET GLU ALA PHE THR GLY ILE PHE ARG SER PRO HIS GLY GLU
     CTT GAT GAT TTC AGA TCC ATG GAA GCA TTT ACA GGA ATC TTC AGA TCA CCA CAT GGG GAA
```

FIG. 3B

```
881
ASP HIS ASP LEU ALA GLY GLU GLU ILE ALA SER TYR SER ILE VAL GLY PRO ALA ASN ALA
GAT CAT GAT CTG GCT GGA GAA GAA ATT GCA TCT TAT TCT ATA GTC GGA CCT GCC AAT GCA

941
LYS VAL PRO HIS SER ALA SER SER ASP THR LEU SER LEU ILE ALA TYR SER GLY ILE PRO
AAA GTT CTT CAT AGT GCT AGC TCA GAT ACA TTG AGC TTG ATT GCC TAT TCA GGT ATA CCA

1001
SER TYR SER SER LEU SER ILE LEU THR SER SER THR GLU ALA LYS HIS VAL PHE SER PRO
TCT TAT TCT TCC CTT AGC ATC CTA ACA AGT TCA ACA GAA GCT AAG CAT GTA TTC AGC CCT

1061                        *
GLY LEU PHE PRO LYS LEU (ASN HIS THR) ASN CYS ASP LYS SER ALA ILE PRO LEU ILE TRP
GGG TTG TTC CCA AAA CTT (AAT CAC ACA) AAT TGT GAT AAA AGT GCC ATA CCA CTC ATA TGG

1121
THR GLY MET ILE ASP LEU PRO GLY TYR TYR GLU ALA VAL HIS PRO CYS THR VAL PHE CYS
ACT GGG ATG ATT GAT TTA CCT GGA TAC TAC GAA GCT GTC CAC CCT TGT ACA GTT TTT TGC

1181                                                              *
VAL LEU SER GLY PRO GLY ALA SER CYS GLU ALA PHE SER GLU GLY GLY ILE PHE (ASN ILE
GTA TTA TCA GGT CCT GGG GCA TCA TGT GAA GCC TTT TCT GAA GGC GGG ATT TTC (AAC ATA

1241
THR) SER PRO MET CYS LEU VAL SER LYS GLN ASN ARG PHE ARG LEU THR GLU GLN GLN VAL
ACC) TCT CCC ATG TGC TTA GTG TCA AAA CAA AAT CGA TTC CGG TTA ACA GAA CAG CAA GTG

1301
ASN PHE VAL CYS GLN ARG VAL ASP MET ASP ILE VAL VAL TYR CYS ASN GLY GLN ARG LYS
AAT TTT GTG TGT CAG CGA GTG GAC ATG GAC ATT GTT GTG TAC TGC AAC GGG CAG AGG AAA

1361
VAL ILE LEU THR LYS THR LEU VAL ILE GLY GLN CYS ILE TYR THR ILE THR SER LEU PHE
GTA ATA TTA ACA AAA ACT CTA GTT ATT GGA CAG TGT ATA TAT ACT ATA ACA AGC TTA TTC

1421
SER LEU LEU PRO GLY VAL ALA HIS SER ILE ALA VAL GLU LEU CYS VAL PRO GLY PHE HIS
TCA TTA CTA CCT GGA GTA GCA CAT TCT ATT GCT GTT GAA TTG TGT GTA CCT GGG TTC CAT

1481
GLY TRP ALA THR ALA ALA LEU LEU VAL THR PHE CYS PHE GLY TRP VAL LEU ILE PRO ALA
GGT TGG GCC ACA GCT GCT CTG CTT GTT ACA TTC TGT TTC GGA TGG GTT CTT ATA CCA GCA

1541
ILE THR PHE ILE ILE LEU THR VAL LEU LYS PHE ILE ALA ASN ILE PHE HIS THR SER ASN
ATT ACA TTT ATC ATA CTA ACA GTC CTA AAG TTC ATT GCT AAT ATT TTT CAC ACA AGT AAT

1601
GLN GLU ASN ARG LEU LYS SER VAL LEU ARG LYS ILE LYS GLU GLU PHE GLU LYS THR LYS
CAA GAG AAT AGG CTA AAA TCA GTA CTT AGA AAG ATA AAG GAA GAG TTT GAA AAA ACA AAA

1661
GLY SER MET VAL CYS ASP VAL CYS LYS TYR GLU CYS GLU THR TYR LYS GLU LEU LYS ALA
GGC TCA ATG GTA TGT GAT GTC TGC AAG TAT GAG TGT GAA ACC TAT AAA GAA TTA AAG SCA

1721
HIS GLY VAL SER CYS PRO GLN SER GLN CYS PRO TYR CYS PHE THR HIS CYS GLU PRO THR
CAC GGG GTA TCA TGC CCC CAA TCT CAA TGT CCT TAC TGT TTT ACT CAT TGT GAA CCC ACA
```

FIG. 3C

```
1781
GLU ALA ALA PHE GLN ALA HIS TYR LYS VAL CYS GLN VAL THR HIS ARG PHE ARG ASP ASP
GAA GCA GCA TTC CAA GCT CAT TAC AAG GTA TGC CAA GTT ACT CAC AGA TTC AGG GAT GAT

1841                              *
LEU LYS LYS THR VAL THR PRO GLN (ASN PHE THR) PRO GLY CYS TYR ARG THR LEU ASN LEU
CTA AAG AAA ACT GTT ACT CCT CAA (AAT TTT ACA) CCA GGA TGT TAC CGG ACA CTA AAT TTA

1901
PHE ARG TYR LYS SER ARG CYS TYR ILE PHE THR MET TRP ILE PHE LEU LEU VAL LEU GLU
TTT AGA TAC AAA AGC AGG TGC TAC ATC TTT ACA ATG TGG ATA TTT CTT CTT GTC TTA GAA

1961                            [G2 >
SER ILE LEU TRP ALA ALA SER ALA SER GLU THR PRO LEU THR PRO VAL TRP ASN ASP ASN
TCC ATA CTG TGG GCT GCA AGT GCA TCA GAG ACA CCA TTA ACT CCT GTC TGG AAT GAC AAT

2021
ALA HIS GLY VAL GLY SER VAL PRO MET HIS THR ASP LEU GLU LEU ASP PHE SER LEU THR
GCC CAT GGG GTA GGT TCT GTT CCT ATG CAT ACA GAT TTA GAG CTT GAT TTC TCT TTA ACA

2081
SER SER SER LYS TYR THR TYR ARG ARG LYS LEU THR ASN PRO LEU GLU GLU ALA GLN SER
TCC AGT TCC AAG TAT ACA TAC CGT AGG AAG TTA ACA AAC CCA CTT GAG GAA GCA CAA TCC

2141
ILE ASP LEU HIS ILE GLU ILE GLU GLU GLN THR ILE GLY VAL ASP VAL HIS ALA LEU GLY
ATT GAC CTA CAT ATT GAA ATA GAA GAA CAG ACA ATT GGT GGT GAT GTG CAT GCT CTA GGA

2201
HIS TRP PHE ASP GLY ARG LEU ASN LEU LYS THR SER PHE HIS CYS TYR GLY ALP CYS THR
CAC TGG TTT GAT GGT CGT CTT AAC CTT AAA ACA TCC TTT CAC TGT TAT GGT GCT TGT ACA

2261
LYS TYR GLU TYR PRO TRP HIS THR ALA LYS CYS HIS TYR GLU ARG ASP TYR GLN TYR GLU
AAG TAT GAA TAC CCT TGG CAT ACT GCA AAG TGC CAT TAT GAA AGA GAT TAC CAA TAT GAG

2321                  *
THR SER TRP GLY CYS (ASN PRO SER) ASP CYS PRO GLY VAL GLY THR GLY CYS THR ALA CYS
ACG AGC TGG GGT TGT (AAT CCA TCA) GAT TGT CCT GGG GTG GGC ACA GGC TGT ACA GCA TGT

2381
GLY LEU TYR LEU ASP GLN LEU LYS PRO VAL GLY SER ALA TYR LYS ILE ILE THR ILE ARG
GGT TTA TAC CTA GAT CAA CTG AAA CCA GTT GGT AGT GCT TAT AAA ATT ATC ACA ATA AGG

2441
TYR SER ARG ARG VAL CYS VAL GLN PHE GLY GLU GLU ASN LEU CYS LYS ILE ILE ASP MET
TAC AGC AGG AGA GTC TGT GTT CAG TTT GGG GAG GAA AAC CTT TGT AAG ATA ATA GAC ATG

2501
ASN ASP CYS PHE VAL SER ARG HIS VAL LYS VAL CYS ILE ILE GLY THR VAL SER LYS PHE
AAT GAT TGT TTT GTA TCT AGG CAT GTT AAG GTC TGC ATA ATT GGT ACA GTA TCT AAA TTC

2561
SER GLN GLY ASP THR LEU LEU PHE PHE GLY PRO LEU GLU GLY GLY GLY LEU ILE PHE LYS
TCT CAG GGT GAT ACC TTA TTG TTT TTT GGA CCG CTT GAA GGT GGT GGT CTA ATA TTT AAA
```

FIG. 3D

```
2621
HIS TRP CYS THR SER THR CYS GLN PHE GLY ASP PRO GLY ASP ILE MET SER PRO ARG ASP
GAC TGG TGT ACA TCC ACA TGT CAA TTT GGT GAC CCA GGA GAT ATC ATG AGT CCA AGA GAC

2681
LYS GLY PHE LEU CYS PRO GLU PHE PRO GLY SER PHE ARG LYS LYS CYS ASN PHE ALA THR
AAA GGT TTT TTA TGC CCT GAG TTT CCA GGT AGT TTC AGG AAG AAA TGC AAC TTT GCT ACT

2741
THR PRO ILE CYS GLU TYR ASP GLY ASN MET VAL SER GLY TYR LYS LYS VAL MET ALA THR
ACC CCT ATT TGT GAG TAT GAT GGA AAT ATG GTC TCA GGT TAC AAG AAA GTG ATG GCG ACA

2801                          *
ILE ASP SER PHE GLN SER PHE (ASN THR SER) THR MET HIS PHE THR ASP GLU ARG ILE GLU
ATT GAT TCC TTC CAA TCT TTT (AAT ACA AGC) ACT ATG CAC TTC ACT GAT GAA AGG ATA GAG

2861
TRP LYS ASP PRO ASP GLY MET LEU ARG ASP HIS ILE ASN ILE LEU VAL THR LYS ASP ILE
TGG AAA GAC CCT GAT GGA ATG CTA AGG GAC CAT ATA AAC ATT TTA GTA ACG AAG GAC ATT

2921
ASP PHE ASP ASN LEU GLY GLU ASN PRO CYS LYS ILE GLY LEU GLN THR SER SER ILE GLU
GAC TTT GAT AAC CTT GGT GAA AAT CCT TGC AAA ATT GGC CTA CAA ACA TCT TCT ATT GAG

2981
GLY ALA TRP GLY SER GLY VAL GLY PHE THR LEU THR CYS LEU VAL SER LEU THR GLU CYS
GGG GCC TGG GGT TCT GGT GTG GGG TTC ACA TTA ACA TGT CTG GTA TCA CTA ACA GAA TGT

3041
PRO THR PHE LEU THR SER ILE LYS ALA CYS ASP LYS ALA ILE CYS TYR GLY ALA GLU SER
CCT ACC TTT TTG ACC TCA ATA AAG GCT TGT GAT AAG GCT ATC TGT TAT GGT GCA GAG AGT

3101
VAL THR LEU THR ARG GLY GLN ASN THR VAL LYS VAL SER GLY LYS GLY GLY HIS SER GLY
GTA ACA TTG ACA AGA GGA CAA AAT ACA GTC AAG GTA TCA GGG AAA GGT GGC CAT AGT GGT

3161
SER THR PHE ARG CYS CYS HIS GLY GLU ASP CYS SER GLN ILE GLY LEU HIS ALA ALA ALA
TCA ACA TTT AGG TGT TGC CAT GGG GAG GAC TGT TCA CAA ATT GGA CTC CAT GCT GCT GCA

3221
PRO HIS LEU ASP LYS VAL ASN GLY ILE SER GLU ILE GLU ASN SER LYS VAL TYR ASP ASP
CCT CAC CTT GAC AAG GTA AAT GGG ATT TCT GAG ATA GAA AAT AGT AAA GTA TAT GAT SAT

3281
GLY ALA PRO GLN CYS GLY ILE LYS CYS TRP PHE VAL LYS SER GLY GLU TRP ILE SER GLY
GGG GCA CCG CAA TGT GGG ATA AAA TGT TGG TTT GTT AAA TCA GGG GAA TGG ATT TCA GGG

3341
ILE PHE SER GLY ASN TRP ILE VAL LEU ILE VAL LEU CYS VAL PHE LEU LEU PHE SER LEU
ATA TTC AGT GGT AAT TGG ATT GTA CTC ATT GTC CTC TGT GTA TTT CTA TTG TTC TCC TTG

3401
VAL LEU LEU SER ILE LEU CYS PRO VAL ARG LYS HIS LYS LYS SER *** CTAAATTCTGTGACT
GTT TTA CTA AGC ATT CTC TGT CCC GTA AGG AAG CAT AAA AAA TCA TAG

3464
ATCCTGTTCTTATGTATAGCTTTAACATATATACTAATTTTTATATTCCAGTATACTCTATCTAACACACTAAAAAAAAT

3544
AGTAGCTTTCTAACCACAAAACTTAGATTCTTCTTCTGTATGATGTCTTAACATCTTGCGGTGTCTACTACTA
```

NUCLEOTIDE SEQUENCES ENCODING THE EXPRESSION OF A HANTAAN VIRUS NUCLEOCAPSID PROTEIN AND G1 AND G2 GLYCOPROTEINS

This is a continuation, of application Ser. No. 07/125,105, filed Nov. 25, 1987, now abandoned.

BACKGROUND OF THE INVENTION

The present invention relates to nucleotide sequences that can be used to produce polypeptides that exhibit the characteristics of the nucleocapsid N protein, or one of two glycoproteins G1 and G2, synthesized by the Hantaan virus. The present invention further relates to a method of producing a Hantaan virus vaccine comprised of at least one of the N protein, $G_1$ and G2.

Each year, hundreds and thousands of people in endemic areas, such as China and Korea, developed infection by Hantaan virus, the etiological agent of Korean hemorrhagic fever, resulting in high morbidity and mortality, not only among the natives in those areas, but also among visitors and service personnel assigned to those areas. In recent years, Hantaviruses have been isolated from rodent populations in endemic and epidemic areas, as well as here in the United States. There is no known cure for such a viral infection, it being generally allowed to run its course until terminated by death or development of natural immunity against the virus.

Because of the extremely infectious nature of the Hantaan virus, containment of this virus for purposes of study poses a special problem. For this reason, it has not been practicable to grow large quantities of live Hantaan virus in the laboratories to extract its immunogenic portions for vaccination purposes. By the same token, detailed information concerning the Hantaan virus has been limited heretofore. Although some information is available about its RNA genome, for example, there is insufficient information available to permit production of viral antigens in the laboratory without propagating the live Hantaan virus. If the nucleotide sequences encoding antigenic portions of the Hantaan virus can be identified, it would be possible to synthesize such antigens in a cell-free system or to genetically-engineer a vaccine. Furthermore, if Hantaan viral infection can be diagnosed at an early stage, for example, by using viral cDNA probes, proper patient management at such a stage may improve prognosis of the disease.

The Hantaan virus belongs to the Hantavirus genus of the Bunyaviridae family. Viruses in this family all possess tripartite, single-stranded, negative-sense RNA species, designated large (L), medium (M) and small (S), respectively, in accordance with their respective molecular weights. Each RNA species is enclosed in its own nucleocapsid structure, but all three RNA species are surrounded by a lipid envelope containing two virus-specific glycoproteins, known as G1 and G2 glycoproteins [see Schmaljohn et al, *J. Infect. Dis.* 148: 1005–1101 (1983) Schmaljohn and Dalrymple, in SEGMENTED NEGATIVE STRAND VIRUSES, R. W. Compans and D. H. Bishop, eds., pp. 117–124 (Academic Press, 1984). The Hantaan virus is negative-sense in that it has to produce a positive-sense, complementary RNA ("cRNA") to act as messenger RNA ("mRNA").

Immunogenic Hantaan viral proteins have been identified by Elliott et al, *J. Gen. Virol.* 65: 1282–1293 (1984), who showed that sera from patients who had recovered from Hantaan virus infection precipitates three Hantaan viral proteins, a nucleocapsid N protein and G1 and G2 glycoproteins. It was not known, however, which of the three RNA species of Hantaan virus, or which segment(s) of such species, encode for each of the N, G1 and G2 proteins.

In the production of immunogenic proteins for vaccination purposes, it is not desirable to include in such vaccines other proteins or substances of unknown effect which may be harmful, e.g., pyrogenic substances. Therefore, to produce immunogenic proteins using genetic engineering techniques, i.e., in vitro techniques to produce DNA molecules containing novel combinations of genes or nucleotide sequences, it is necessary to know precisely which segment of a genome encodes the desired protein. The uncertainty with regard to which segments of the Hantaan viral genome encode the desired proteins can be more fully appreciated by considering what is known about viruses of the Bunyavirus and Phlebovirus genera, other members of the Bunyaviridae family. The Bunyaviruses S-RNA molecules utilize an overlapping reading frame strategy in its cRNA to encode a nucleocapsid N protein and a non-structural ("NS$_S$") protein. See Fuller et al, *J. Gen. Virol.* 64: 1705–1714 (1983). In other words, if the nucleotide sequence for the CRNA of S-RNA species is represented by the formula 1-2-3-4-5-6-7-8-9-10, the nucleotide sequence encoding the N protein may be represented by the sequence 1-2-3-4-5-6, while the sequence encoding for the NSS protein may be represented by 3-4-5-6-7-8. Therefore, to produce only the N protein of Bunyavirus by genetic engineering techniques, the sequence 1-2-3-4-5-6, but not 7-8, will have to be present.

On the other hand, viruses of the Phlebovirus genus utilize an ambisense coding strategy in their S-RNA: a N protein is encoded by a nucleotide sequence at the 5' end of the cRNA molecule, and a NS$_S$ protein is encoded by a nucleotide sequence at the 5' end of the viral RNA molecule. Synthesis of the N protein by genetic engineering techniques in this instance will require the presence of a nucleotide sequence comprising the 3' end of the viral RNA molecule, while synthesis of the NS$_S$ protein would require the presence of the 5' and of the viral RNA molecule.

In contrast, studies to date on viruses of the Phlebovirus and Bunyavirus genera revealed that a single long open-reading-frame (ORF) coding strategy was employed in their CRNA complementary to M-RNA to encode single gene products comprising both G1 and G2 glycoproteins. In the Bunyaviruses, the M-RNA additionally encodes for a NS$_M$ ("non-structural$_M$") polypeptide. In the Phleboviruses, sufficient coding information was found which could produce a NS$_M$ polypeptide, but such polypeptide has not been identified in infected cells. To obtain G1 and G2 glycoproteins but not the NS$_M$ proteins, therefore, the specific nucleotide sequence encoding G1 and G2 glycoproteins will have to be identified so that the sequence encoding for NS$_M$ protein can be excluded.

Based upon the present state of the art, it has been impossible to predict a Priori what coding strategy is utilized in the Hantaan virus, and which segments of its genome comprise the nucleotide sequences that encode the polypeptides corresponding to the immunogenic N protein, and G1 and G2 glycoproteins. In order to produce such proteins without the use of live viruses, however, this information is needed to avoid the production of undesirable proteins.

SUMMARY OF THE INVENTION

It is therefore an object of the present invention to identify the nucleotide sequences that can be expressed to obtain polypeptides exhibiting the characteristics of a Hantaan virus nucleocapsid (N) protein or of a G1 or G2 glycoprotein.

It is a another object of the present invention to provide a method of producing immunogenic proteins of Hantaan virus, without the need to propagate live Hantaan viruses.

In accomplishing these and other objects, there has been provided in accordance with one aspect of the present invention, a vector comprising at least one nucleotide sequence selected from the group consisting of a sequence coding for a first polypeptide exhibiting the characteristics of a Hantaan virus nucleocapsid protein and a sequence coding for a second polypeptide that is a precursor of a Hantaan virus glycoprotein. In one preferred embodiment, a vector comprises a nucleotide sequence as described above and a DNA plasmid, pGem 1, which is comprised of a promoter sequence for SP6 polymerase.

In accordance with another aspect of the present invention, there has been provided a cDNA molecule comprising at least one of the abovementioned nucleotide sequences.

In accordance with yet another aspect of the present invention, there has been provided a method of producing a Hantaan virus WWA molecule comprising the step of transcribing a cDNA molecule described above.

In accordance with still another aspect of the present invention, a method of producing a vaccine comprises the steps of translating a Hantaan virus mRNA molecule, as described above, and of purifying a resultant translation product, has been provided.

Further objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
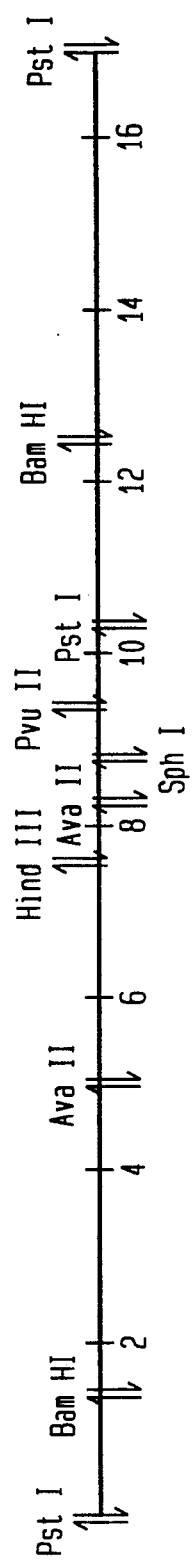
FIG. 1 is a partial restriction map corresponding, from left to right, to Hantaan virus complementary RNA 5'-3'. The numbers represent nucleotide positions $\times 100$.

It has been discovered that the Hantaan virus utilizes a single long open-reading-frame (ORF) coding strategy, in both its CRNA complementary to S-RNA and cRNA complementary to M-RNA, to encode a single polypeptide which exhibits the characteristics of its nucleocapsid protein and a single polypeptide that is a precursor of the G1 and G2 glycoproteins, respectively. The term "precursor" is used here to denote a polypeptide that is cleaved and glycosylated before it has the characteristics of G1 and C2 glycoproteins. In contrast to other members of the Bunyaviridae family, Hantaan virus S-RNA does not encode a $NS_S$ protein, and its M-RNA does not encode a $NS_M$ protein.

Based upon the discovery of Hantaan virus' coding strategy, cDNA molecules comprising nucleotide sequences that encode viral nucleocapsid protein and glycoproteins can now be constructed and inserted into vectors. A vector in the context of the present invention comprises a first DNA molecule comprising at least one restriction site, e.g., plasmid pGem 1, and a second DNA molecule which can be inserted into said restriction site, e.g., Hantaan virus cDNA, wherein the vector is capable of infecting or transforming a host cell, and of autonomous replication in a host cell or. of employment of a host's enzyme systems for its replication. A restriction site within the present invention comprises a specific nucleotide sequence recognizable by a type II restriction endonuclease and within which it makes a cut in the DNA. Vectors suitable for use in the present invention are described by Maniatis et al, in MOLECULAR CLONING: A LABORATORY MANUAL, Cold Spring Harbor Laboratory, N.Y. (1982), and includes, for example, plasmids pGem 1 and pBR322, and bacteriophage M13.

A cDNA molecule according to the present invention can be made in accordance with generally known laboratory procedures using enzyme reverse transcriptase, Hantaan viral RNA genome as template and a synthetic oligonucleotide as primer. The synthetic oligonucleotide is complementary to the first 17-19 bases at the 3' end of the viral RNA, and is made by the use of a DNA synthesizer, Model 381A, Applied BioSystems, Inc. (San Francisco, CA) in accordance with the manufacturer's directions according to the phosphoramidite method of oligonucleotide synthesis, and based upon the terminal sequence information previously obtained, see Schmaljohn and Dalrymple (1983). Hantaan virus RNA can be extracted in the manner described in detail below. After incubation, the reaction is terminated and the RNA template is degraded. The resultant single-stranded cDNA can be converted into a double-stranded DNA, for example, by the use of DNA polymerase as in the method of Maniatis et al, loc. cit.

A cDNA molecule within the present invention can further comprise at least one of a leader sequence and a tail sequence that are, respectively, a nucleotide sequence that precedes and a nucleotide sequence that follows the sequences for encoding N protein or the precursor of the G1 and G2 glycoproteins. The leader and tail sequences may provide necessary sites upon which enzymes such as endonuclease can act, or may function as a buffer such that, in inserting or removing a desired sequence, the desired sequence itself is not cleaved. In general, the length and the specific nucleotide sequence of leader and/or tail sequence is not crucial so long as the above-mentioned functions are not impaired. In the case of the precursor for G1 and G2 glycoproteins, however, a leader sequence that encodes hydrophobic proteins may be necessary for proper processing of the glycoproteins when they are synthesized in rabbit reticulocyte lysate systems, as described in detail below.

Vectors comprised of Hantaan virus cDNA within the present invention, can be made by inserting double-stranded cDNA of Hantaan virus into replicative forms of plasmids of bacterial origin or into DNA of bacteriophages. Insertion of cDNA can be accomplished, for example, by dC-tailing the cDNA from Hantaan virus and dg-tailing the DNA of the plasmid, and circularizing the recombined plasmid by annealing the "sticky ends" created in this manner, e.g., with the use of ligase.

Examples of a vector comprising a cDNA molecule that encodes a Hantaan virus nucleocapsid N protein, and of a vector comprising a cDNA molecule that encodes a polypeptide that is a precursor of G1 and G2 glycoproteins, are deposited with the American Type Culture Collection (ATCC), 12301 Parklawn Drive, Rockville, Maryland 20852, U.S.A., under accession Nos. 67675 and 67676, respectively.

Vectors made in this way can be used to transform a host cell, for example, *Escherichia coli*, K-12, strain HB101, which can produce one or more copies of such vectors during each replicative cycle. A host cell can be rendered susceptible to transformation by plasmid, for example, by treatment with calcium chloride. Transformed host cells are then plated on a medium selective for the plasmid, e.g., on a medium comprising tetracycline to select for a tetracycline-resistance determinant carried by plasmid pBR322. Identification of bacterial colonies comprising the Hantaan virus DNA is performed by first transferring the resultant bacterial colonies to multiple plates and replicate filters (Whatman 541), as described, for example, by Grunstein and Hogness, *Proc. Natl. Acad. Sci. USA*, 72: 3961–3965 (1975), and then probing such filters either with the same synthetic oligonucleotide as used for priming the first strand cDNA synthesis, but phosphorylated at the 5' ends with $\gamma$-ATP$^{32}$, or with cDNA probes prepared from gel-purified S-RNA or M-RNA primed with random DNA primers.

The Hantaan virus cDNA molecule can be moved from one vector to another to suit the purpose. For example, cDNA inserted into plasmid pBR322 can be excised by partial digestion with PstI, purified by agarose gel electrophoresis and subcloned into M13 bacteriophage for sequencing or into the ERI site of the pGem 1 plasmid (Promega Biotec), which comprises a SP6 promotor, for purpose of synthesizing RNA.

To produce mRNA from cDNA within the present invention, the plasmid comprising Hantaan virus cDNA can be linearized at unique restriction sites adjacent to the cloning site, that is, the site of insertion of cDNA, and RNA can be transcribed using a DNA-dependent RNA polymerase. In particular, plasmid pGem 1 comprising Hantaan viral cDNA can be linearized at unique XbaI or SAlI restriction sites adjacent to the PstI cloning site, and RNA can be synthesized by addition of SP6 polymerase (Promega Biotec), used in accordance with manufacturer's directions. The mRNA molecules produced in this manner can be purified by known laboratory techniques.

mRNA generated in accordance with the present invention can be used to program cell-free rabbit reticulocyte lysate translation systems to generate Hantaan viral proteins. The resultant proteins can be purified by immune-precipitation using antisera prepared against whole virions, by adsorption to a column comprising such antisera, or by polyacrylamide gel electrophoresis, in accordance with known laboratory techniques.

Antisera against Hantaan virus or its immunogenic proteins within the present invention can be obtained from ascitic fluid of mice hyper-immunized with Hantaan virus or its N, G1 or G2 proteins and subsequently injected with Sarcoma 180 cells, in accordance with the method of Brandt et al, *Amer. J. Trop. Med. Hyg.* 16: 339–347 (1967). In particular, adult female ICR mice are injected both subcutaneously and intramuscularly on days 0, 3 and 28 with a suspension of suckling mouse brains of sick and moribund mice previously inoculated with Hantaan virus strain ATCC VR-938. Sarcoma 180 cells are then injected and ascitic fluid is collected ten to fourteen days after final inoculation of Hantaan virus. From the hyperimmunized mice can be drawn ascitic fluid comprising antibodies against Hantaan virus or its proteins, which fluid is pooled and clarified by centrifugation. Antibody titer in the ascitic fluid can be assayed by plaque-reduction neutralization, hemagglutination inhibition, and radioimmune assay.

The present invention is further described below by reference to the following example.

EXAMPLE 1

Analysis and characterization of a Hantaan virus nucleotide sequence which encodes a polypeptide exhibiting the characteristics of a nucleocapsid N protein.

It was found that Hantaan virus utilized a single long ORF coding strategy in its cRNA complementary to viral S-RNA to encode a single polypeptide that exhibited the characteristics of Hantaan virus nucleocapsid N protein. The reading frame for this polypeptide was found to begin at the 37th nucleotide from the 5' end and to terminate at the 370th nucleotide from the 3' end, see Schmaljohn et al, *Virol.* 155: 633–643 (1986), the contents of which are hereby incorporated by reference.

A cDNA molecule in accordance with the present invention, when inserted into a plasmid, e.g., pGem 1, was found to be capable of encoding RNA which could be translated to produce polypeptides indistinguishable from Hantaan virus N protein by polyacrylamide gel electrophoresis and by specific immune-precipitation using polyclonal, anti-Hantaan sera or monoclonal antibodies directed against Hantaan virus N protein. These polypeptides have a molecular weight of about 48,100, consistent with its predicted molecular weight of about 50,000 daltons. The polypeptide predicted on the basis of the nucleotide sequence was approximately 429 amino acids long.

A. Propagation of Hantaan Virus In Vitro

Hantaan virus, strain ATCC VR-938, was propagated in Vero E6 cells (ATCC No. C1008), purified, and its total RNA extracted in accordance with the procedure in Schmaljohn et al (1983). Essentially, the virus was propagated in E6 cells, at multiplicities of infection of less than 0.1, in 30 ml of growth medium comprised of Eagle's minimal essential medium containing Earles' salts, 10% heated fetal bovine serum, 100 units of penicillin, 100 µg/ml of streptomycin, 0.5 µg/ml of Fungizone ®, (Gibco, Grand Island, NY) and 60 μg/ml of Tylocine ® (Gibco), in 150-cm² plastic tissue culture flasks and incubated at 37'C. viruses from a second Vero E6 passage were used for isolation of RNA. Growth medium was removed 4 days post-infection and replaced with fresh growth medium. Infected cell culture supernatants were harvested 8 days post-infection, and clarified by centrifugation for 30 minutes at 7,900 g at 4'C in a Sorvall GSA rotor (Dupont, Newtown, CT). The virus in the supernatant was concentrated by polyethylene glycol precipitation by adding solid polyethylene glycol 6,000 (Sigma Chemical Co., St. Louis, MO) to a final concentration of 8% and sodium chloride to a final concentration of 0.5M, stirring the mixture for 4 hours at 4'C, and collecting the precipitated virus by centrifugation at 7,900 g, for 30 minutes in a Sorvall GSA rotor. Pellets were resuspended in a mixture of 0.01M Tris, 0.1M NaCl, and 0.001M EDTA (hereafter referred to as "TNE"), pH 7.4, then layered on a 10%–60% sucrose-TNE gradient and centrifuged for 2-24 hours in a model SW-41 (Beckman Instruments, Cedar Crove, NJ) at 195,000 g. Fractions from the sucrose gradient were collected, and virus-containing fractions were identified by scintillation counting of radiolabeled virus, or solid-phase radioimmune assay ("RIA"), as described below.

For radiolabeling of Hantaan virus, infected E6 cell cultures were radiolabeled from four to eight days after infection with one of ($^{35}$S)methionine at 10 μCi/ml, $^3$H-labeled mixed amino acids, at 10 μCi/ml, [$^3$H]uridine at 30 μCi/ml, or ($^{32}$P)orthophosphate at 150 μCi/ml.

For solid-phase RIA, known laboratory methods can be employed, for example, as described by Schmaljohn et al, (1983). In particular Hantaan virus antiserum used for antigen detection was a 1 in 50 dilution of recalcified plasma from a convalescent patient who acquired clinical Korean Hemorrhagic fever while living in Korea. Protein A (Pharmacia, Piscataway, NJ) iodinated with $^{125}$I (Amersham, Arlington Heights, IL) by chloramine T method was used to detect human IgG. Viral titer was assayed by plaque formation on Vero E6 monolayers with the use of an overlay consisting of 0.6% agarose in the growth medium. The monolayers were incubated for eight to ten days prior to neutral red staining.

B. Extraction of Hantaan Virus RNA

To extract Hantaan virus RNA, viruses prepared above were placed in TNE containing 1% SDS, and an equal volume of a saturated solution of TNE in a solution comprising 500 ml of phenol, 70 ml of cresol, and 0.5 g of 8-hydroxy-quinoline was added to the viruses. Total viral RNA was recovered in the aqueous phase following centrifugation at 13,400 g in a Sorvall HB-4 rotor (Difco) for 10 minutes, reextracted with the above-mentioned phenol solution, and precipitated with cold ethanol and 0.3M sodium acetate. RNA extracted in this manner was used either directly as template for cDNA synthesis or was separated into L-, M- and S-RNA species prior to such use. Separation of RNA species was accomplished by dissolving RNA in 10 mM sodium phosphate, pH 7.0, and subjecting the solution to horizontal agarose gel electrophoresis on a subcell electrophoresis unit (Bio-Rad Laboratories, Richmond, CA) for 8 to 12 hours at 40 V. The agarose gels consisted of 1.4% SeaPlaque ® agarose (Marine Colloids, Rockland,, ME), 10 mM sodium phosphate, pH 7.0.

C. Generation of cDNA

First-strand cDNA was synthesized in a DNA synthesizer, as described above, using the viral RNA extracted above as a template and, as a primer, a synthetic oligonucleotide, 5'-TAGTAGTAGACTCCCTA-3', complementary to 17 bases at the 3' end of Hantaan virus S-RNA, as described above. In particular, approximately 50 μg of total virion RNA in water and 1 μg of primer were incubated at room temperature for 10 minutes in the presence of methylmercury hydroxide, at 10 mM final concentration (Alfa Biochemicals, Denvers, MA). The RNA/primer mixture in approximately 5.5 μl was then treated with 1 μl of 700 mM 2-mercaptoethanol (Sigma) and added to a reaction mixture containing:

(a) 3 μl of 2.5 mM of each of dATP, dCTP, dGTP and DTTP (Pharmacia, Piscataway, N.J.), (b) 3 μl of a 5X buffer comprising 250 mM Tris-HCl, pH 8.3, 50 Mm 50 MgCl$_2$, 50 mM dithiothreitol, 350 Mm KCl, (c) 1 μl of RNAsin (Promega Biotec, Madison, WI), and (d) 1.5 μl of AMV reverse transcriptase (15 units/μl, Life Sciences, Inc., St. Petersburg, FL).

The combined mixture was incubated for 2 hours at 42'C, and the reaction terminated by addition of 2 μl of 0.5M EDTA, pH 8.0. The RNA template was then degraded by incubating the cDNA/RNA complex in 150 Mm N2OH at 65'C for 1 hour. Single stranded cDNA was recovered by ethanol precipitation.

D. Production of Vectors

Single-stranded DNA prepared as described above was converted to double-stranded DNA with the large fragment of DNA polymerase I (Pharmacia) in accordance with known laboratory procedures. After S1 nuclease treatment and dC tailing, cDNA was annealed to PstI-cleaved, dG-tailed pBR322 (New England Nuclear, Boston, MA). The annealed plasmid was used to transform *Escherichia coli* K-12, strain HB101, which was then plated on Luria-Bertani agar plates containing 20 μ/ml of tetracycline. Resultant bacterial colonies were transferred to multiple plates and replicate filters (Whatman 541). Bacterial colonies which contained Hantaan virus cDNA were identified by probing the filters either with the same synthetic oligonucleotide as used for priming first-strand cDNA synthesis, except for being phosphorylated at the 5' ends with γ-ATP$^{32}$, or with radiolabeled cDNA probes prepared from gel-purified S-RNA and random DNA primers.

E. Identification of Nucleotide Sequence.

Figure 2:
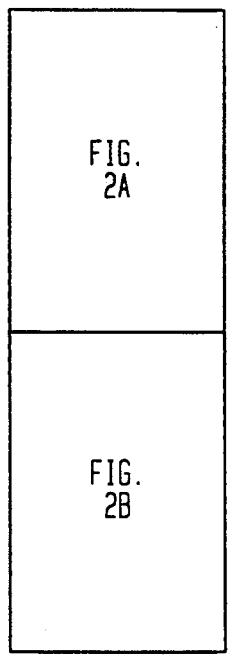
FIG. 2 (which is composed of FIGS. 2A, and 2B) is Hantaian virus S-RNA nuclitidesequences presented as the viral complementary DNA strand, 5'-3'. Nucleotides are numbered on the left end of each line and predicted amino acids for the major open-reading-frame are positioned above their codons.

Nucleotide sequence of Hantaan virus cDNA were identified as described above. Three clones of cDNA, S8, S16 and S86 which appeared of sufficient length to encompass most or all of Hantaan virus S-RNA were selected for restriction mapping. and sequence analysis. The sequence S8 was determined both by chemical cleavage method of Maxam and Gilbert (1980), and by the dideoxy chain termination method of Sanger et al (1977). S16 and portions of S86 were sequenced by the dideoxy method with M13 specific primers. Nucleotide sequence determined by these methods can be analyzed manually or with the aid of a computer using known programs, for example, Intelligenetics sequence-analysis program or University of Minnesota sequence-analysis program, to generate information regarding, e.g., composite sequence of S-RNA and M-RNA, restriction enzyme cleavage sites, and glycosylation sites. A partial restriction map of Hantaan virus S-RNA is shown in FIG. 1. A consensus nucleotide sequence of S8, S16 and S86 is shown in FIG. 2.

Clone S86 was found to have complementary sequences in its 5' and 3' terminals which included 20 of the terminal 22 nucleotides. Since viruses of the Bunyaviridae family generally have terminal nucleotide complementarity, S86 is believed to comprise a complete copy of the S segment of Hantaan virus.

F. Generation of mRNA from cDNA.

For generation of mRNA, the genetically-engineered vector described above, comprising pGem 1 plasmid and Hantaan virus cDNA, was used to transform a bacterial host, *E. coli*, K-12, strain HB101, and the transformed host was propagated to generate multiple copies of such vectors. Vectors were separated from host DNA after lysis of cells, for example, by lysozyme treatment or treatment on ice in a lysis buffer containing 10 mM Tris-HCl, pH 8.0, 1 mM EDTA, 0.5M NaCl, 0.25 mg/ml each of aprotinin and $\alpha_2$-macroglobulin (Sigma) and 4% Zwittergent 3-14 (Calbiochem-Behring, San Diego, CA). Cell nuclei and cellular debris were removed by centrifugation at 13,000 g for 5 minutes at 4'C. The supernatant was then subjected to agarose gel electrophoresis. The vectors thus obtained were linearized at unique XbaI or SAII restriction sites adjacent to the PstI cloning site. SP6 was added to the linearized vectors for transciption of RNA from DNA, in accordance with manufacturer's directions (Promega Biotec). The cDNA templates were then digested.

G. Cell-Free Translation of RNA

RNA generated from Hantaan virus cDNA as described above was used to program a cell-free translation system. Although a rabbit reticulocyte lysate was used for this purpose, any cell-free system is suitable if it is capable of supporting the cleavage and glycosylation of the precursor polypeptide, thereby to generate G1 and G2. Such suitable lysate systems are commercially available (e.g., from New England Nuclear, Promega Biotec, Amersham, and Bethesda Research Laboratories, among others) and can be used in accordance with manufacturer's directions. Resultant polypeptides can be purified by generally known laboratory methods.

No demonstrable products were translated from RNA in the virion orientation, but numerous translation products could be identified when lysates were programmed with RNA transcripts in the Hantaan virus CRNA orientation. The largest and most abundant translation product was found by polyacrylamide gel electrophoresis, as described below, to be indistinguishable from N protein isolated from Hantaan virus. This polypeptide could be immune-precipitated using the above-described polyclonal, anti-Hantaan sera or monoclonal antibodies directed against Hantaan N protein. A variety of smaller products, presumably formed from premature termination of translation, were occasionally precipitated from translation mixtures. No polypeptides other than Hantaan virus N protein, however, were specifically and consistently immune-precipitated.

H. Polyacrylamide Gel Electrophoresis ("PAGE") of Viral Proteins

Viral proteins were obtained from lysis of Vero E6 cells about eight days after infection of such cells with Hantaan virus. Cells were lysed on ice in a lysis buffer and cell nuclei and cellular debris were removed as described above. Virus-specific proteins were immune precipitated from infected cell lysates by incubation with antisera on ice overnight followed by the addition of 100 $\mu$l of 50% protein A-Sepharose (Sigma) and continued incubation for 30 minutes. Precipitates were washed three times in 1 in 2 dilution of the lysis buffer described above, and once in 10 Mm Tris-HCl, pH 6.7. Electrophoresis was performed at 100 V for 12 hours in SDS-containing polyacrylamide gels, for example, as disclosed by Laemmli, *Nature* 227: 680-685 (1970). In particular, viral proteins were dissociated by addition of an equal volume of 0. 5M Tris-HCl , pH 6.7, containing 5% SDS and 4% -mercaptoethanol. These samples were boiled for 2 minutes prior to electrophoresis. Electrophoresis was conducted in discontinuous gels comprising acrylamide:N,N'diallyltartardiamide (DATD), at a ratio of 30:1.41, at 100 V for about 5 hours in a 0.025M Tris and 0.2M glycine buffer, at pH 8.3. The resolving gel consisted of 12% acrylamide:DATD, 0.1% SDS, and 0.375M Tris-HCl , pH 8.9. The stacking gel consisted of 3.6% acrylamide:DATD, 0.1% SDS, and 0.062M Tris-HCl , pH 6.7.

EXAMPLE 2

Analysis and characterization of a Hantaan virus nucleotide sequence which encodes a polypeptide that is a precursor of G1 and G2 glycoproteins It was found that Hantaan virus utilized a single long ORF coding strategy in its CRNA complementary to viral M-RNA to encode a single polypeptide that is a precursor of Hantaan virus glycoproteins G1 and G2. It was further found that protein synthesis began at nucleotide positions 41-43 and terminated at nucleotide positions 3446-3448, encoding a total of 1135 amino acids, see Schmaljohn et al, *Virol.* 157: 31-39 (1987), the contents of which are hereby incorporated by reference. It was also found that this polypeptide comprised a precursor of both G1 and G2 glycoproteins, the gene sequence being 5'-G1-G2-3'. It is not known, however, how this polypeptide is cleaved to generate G1 and G2 glycoproteins. The amino acid sequence of G1 was found to extend at least from amino acid 19 to include amino acids 588-614 while the amino acid sequence of G2 was found to extend from amino acid 649 to include amino acids 1127-1135. Seven putative glycosylation sites, predicted on the basis of amino acid sequence Asn-X-ser/Thr, where X represents any amino acid, are indicated by parentheses and an * in FIG. 3. G1 was found to have a molecular weight of about 64,000 daltons, while G2 was found to have a molecular weight of about 54,000 daltons, close to its predicted values of 62 K and 52 K, respectively.

A. Generation and Sequence Analysis cDNA

Hantaan virus was propagated in Vero E6 cells and virion RNA extracted as in Example 1 above. First strand cDNA synthesis was accomplished as in Example 1 except the synthetic oligonucleotide used was 5'-TAGTAGTAGACTCCGCAAA-3', complementary to nineteen bases at the 3' end of virion M-RNA. Double-stranded cDNA was synthesized, tailed, and inserted into the PstI site of pBR322, and recombinant plasmids were identified as in Example 1, except that the transformed bacterial colonies were probed with radiolabeled cDNA prepared from gel-purified M-RNA. Sequence analysis of the cDNA molecules was performed by the dideoxy chain termination method of Sanger et al (1977), using cDNA subcloned into bacteriophage M13 as templates and synthetic oligonucleotides complementary to portions of M13 and/or such cDNA as primers. Sequence data were analyzed as described above.

Comparison of the 5' and 3' terminals of a large cDNA clone complementary to virion M-RNA showed complementary sequences for eighteen bases including all but the three most distal nucleotides complementary to the virion RNA sequence. Since 3' and 5' complementarity is a general feature of Bunyaviridae family, this clone was believed to represent the entire M-RNA segment except for six bases corresponding to the 3' terminus and three bases corresponding to the 5' terminus of virion RNA. A base composition for the entire virion M-RNA was determined from cDNA sequence information to be 29.9% A, 17.9% G, 21.4% C, and 30.8% U.

Figure 3:
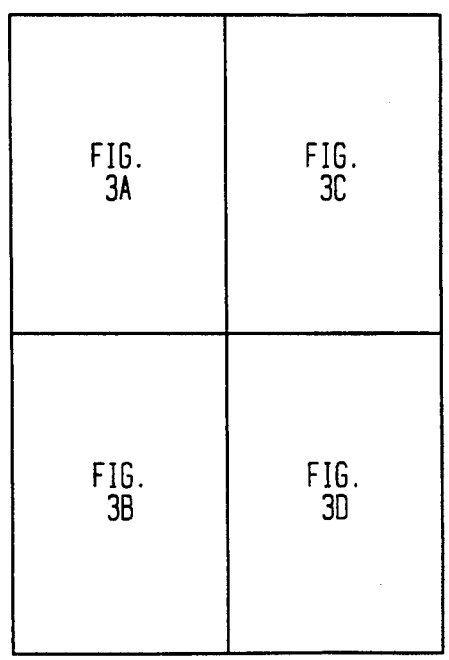
FIG. 3 (which is composed of FIGS. 3A, 3B, 3C and 3D) is shown on two pages and represents Hantaan virus M-RNA nucleotide sequences presented as the viral complementary DNA strand, 5'-3'. Nucleotide are numbered on the left end of each line and predicted amino acids for the major open-reading-frame are positioned above their codons. Anino terminal of each of G1 and G2 is indicated by a bracket and an arrow.

A single long ORF was detected in the nucleotide sequence complementary to viral CRNA. The nucleotide sequence of a large clone of cDNA complementary to viral M-RNA was identified, as shown in FIG. 3.

B. Gneeration of RNA and G1 and G2 Glycoproteins

Hantaan viral mRNA was generated from cDNA complementary to M-RNA in the same manner as described in Example 1. This mRNA was also similarly translated in rabbit reticulocyte lysate translation systems. The resulting proteins were purified by precipitation with antisera or by polyacrylamide gel electrophoresis, in accordance with known laboratory procedures. A total of 1135 amino acids were encoded from the first ATG until a termination codon, TAG, occurred at nucleotide position 3446-3448. Gene order, determined by partial amino acid analysis of the amino-terminal of G1 and G2, as described below, was found to be 5'-G1-G2-3'.

C. Amino-terminal Sequence Analysis of G1 and G2

To determine the gene order of the Hantaan virus M-RNA and to locate the amino terminals of G1 and G2, viral G1 and G2 glycoproteins were isolated and subjected to amino-terminal sequence analysis. These glycoproteins were prepared for amino-terminal sequence analysis by electrophoresis through polyacrylamide gels in accordance with known laboratory techniques. In particular, proteins were boiled in 65 mM Tris-borate, pH 8.4, containing 1% SDS, 5% 2-mercaptoethanol, and 10% glycerol and applied to a 3 mm-thick, discontinuous, polyacrylamide gel. A 60-ml separating gel of 10% acrylamide and 0.05% bisacrylamide was prepared in 0.17M Tris-sulfate, pH 8.4. Gels were allowed to polymerize for at least 24 hours and were electrophoresed at 100 V for approximately 12 hours, after which they were sliced horizontally. Proteins were recovered from gel slices by agitation in 50 Mm ammonium bicarbonate containing 0.1% SDS for two separate 12-hour periods. Samples were lyophilized and dialyzed extensively against water. Approximately 100 pmol of purified proteins was sequenced on Model 470A protein sequencer (Applied Biosystems Inc.) and analyzed with a 120A on-line PTH analyzer. A partial amino acid sequence of (NH2)-Leu-X-X-Val-Tyr-Asp-Met-Lys-Ile-Glu-X-Pro-His-Thr -Thr-Val was determined for G1 and (NH2)-X-Glu-X-Pro -Leu-X-Pro-Val-Trp-Asn-Asp-Asn-Ala-His-Gly-val-Gly for G2, where X represented unidentified amino acids. These sequences were found to correspond to those derived from cDNA beginning at nucleotide positions 95-97 for G1 and 1985-1987 for G2, therefore, establishing the gene order of M-RNA as 5'-G1-G2-3'.

The carboxy terminal of G1 and G2, respectively, was identified by synthesizing peptides, corresponding to amino acids 588-614, i.e., NH2-Tyr-Lys-Val-Cys-Gln-Val-Thr-His-Arg-Phe-Arg-Asp -Asp-Leu-Lys-Lys-Thr-Val-Thr-Pro-Gln-Asn-Phe-Thr-Pro-Gly-Cys-COOH, and 1127-1135, i.e., NH2-Cys-Pro-Val-Arg-Lys-His-Lys-Lys-Ser-COOH, of the ORF respectively, as described below, injecting such polypeptides into rabbits to generate antisera and testing, by immune precipitation, the ability of the antisera to recognize G1 and G2 extracted from Hantaan virus.

D. Peptide Synthesis and Immune Precipitation

Peptides representing derived amino acid sequences were synthesized with an Applied Biosystems, Inc. Model 430A peptide synthesizer. Peptides were cleaved from the resin with hydrofluoric acid and coupled to keyhole limpet hemocyanin.

Approximately 1–1.5 mg of each coupled peptide was injected intradermally with Freund's complete adjuvant into four shaved sites on each of two young female New Zealand white rabbits. Rabbits were boosted with approximately 1.5 mg of coupled peptides in Freund's incomplete adjuvant at 2-week intervals and bled from 10 to 14 days post-boost. Rabbit sera were preadsorbed with uninfected Vero E6 cells prior to use in Hantaan immune-precipitation experiments. Polyclonal rabbit antisera consisted of convalescent sera collected 4–12 weeks following infection of New Zealand white rabbits with Hantaan virus, strain 76–118.

For immune precipitation, intracellular viral proteins were radiclabeled with [$^{35}$S]methionine, at 100 $\mu$Ci per 25-cm$^2$ flask of confluent Vero E6 cells, from 24 to 48 hours post-infection and isolated as described above.

What is claimed is:

1. A vector comprising a nucleotide molecule selected from the group consisting of a nucleotide molecule coding for a Hantaan virus nucleocapsid N protein and a nucleotide molecule coding for a precursor of Hantaan virus G1 and G2 glycoproteins.

2. A vector as claimed in claim 1, wherein said nucleotide molecule coding for said neclocapsid N protein is defined by the formula:

ATG GCA ACT ATG GAG GAA TTA CAG AGG GAA ATC

AAT GCC CAT GAG GGT CAA TTA GTG ATA GCC AGG CAG AAG GTG AGG GAT GCA GAA AAA CAG

TAT GAA AAG GAT CCA GAT GAG TTG AAC AAG AGA ACA TTA ACT GAC CGA GAG GGC GTT GCA

GTA TCT ATC CAG GCA AAA ATT GAT GAG TTA AAA AGG CAA CTG GCA GAT AGG ATT GCA ACT

GGG AAA AAC CTT GGG AAG GAA CAA GAT CCA ACA GGG GTG GAG CCT GGA GAC CAT CTG AAA

GAG AGG TCA ATG CTC AGT TAT GGT AAT GTG CTG GAT TTA AAC CAT TTG GAT ATT GAT GAA

CCT ACA GGA CAG ACA GCA GAC TGG CTG AGC ATC ATC GTC TAT CTT ACA TCC TTT GTC GTC

CCG ATA CTT CTG AAA GCT CTG TAT ATG TTG ACA ACA AGG GGG AGG CAA ACT ACC AAG GAT

AAT AAA GGG ACC CGG ATT CGA TTT AAG GAT GAT AGC TCG TTC GAG GAT GTT AAC GGT ATC

-continued

```
CGG AAA CCA AAA CAT CTT TAC GTG TCC TTG CCA AAT GCA CAG TCA AGC ATG AAG GCA GAA
GAG ATT ACA CCT GGT AGA TAT AGA ACA GCA GTC TGT GGG CTC TAC CCT GCA CAG ATT AAG
GCA CGG CAG ATG ATC AGT CCA GTT ATG AGT GTA ATT GGT TTT CTA GCA TTA GCA AAG GAC
TGG AGT GAT CGT ATC GAA CAA TGG TTA ATT GAA CCT TGC AAG CTT CTT CCA GAT ACA GCA
GCA GTT AGC CTC CTT GGT GGT CCT GCA ACA AAC AGG GAC TAC TTA CGG CAG CGG CAA GTG
GCA TTA GGC AAT ATG GAG ACA AAG GAG TCA AAG GCT ATA CGC AGC ATG CAA AGA GCT
GGC TGT AGC ATG ATT GAA GAT ATT GAG TCA CCA TCA TCA ATA TGG GTT TTT GCT GGA GCA
CCA GAC CGT TGT CCA CCA ACA TGT TTG TTT ATA GCA GGT ATT GCT GAG CTT GGG GCA TTT
TTT TCC ATC CTG CAG GAC ATG CGA AAT ACA ATC ATG GCA TCT AAG ACA GTT GGA ACA TCT
GAG GAG AAG CTA CGG AAG AAA TCA TCA TTT TAT CAG TCC TAC CTC AGA AGG ACA CAA TCA
ATG GGG ATA CAA CTA GGC CAG AGA ATT ATT GTG CTC TTC ATG GTT GCC TGG GGA AAG GAG
GCT GTG GAC AAC TTC CAC TTA GGG GAT GAT ATG GAT CCT GAG CTA AGG ACA CTG GCA CAG
AGC TTG ATT GAT GTC AAA GTG AAG GAA ATC TCC AAC CAA GAG CCT TTG AAA CTC TAA.
```

3. A vector as claimed in claim 2, wherein said nucleotide molecule coding for said nucleocapsid N protein further comprises at least one of (a) a leader-sequence that precedes said nucleotide molecule coding for said nucleocapsid N protein, wherein said leader-sequence comprises a sequence defined by the formula:

TAGTAGTAGACTCCCTAAAGAGCTAC-
TAGAACAACG, and (b) a tail-sequence that follows said nucelotide molecule coding for said nucleocapsid N protein, wherein said tail-sequence comprises a sequence defined by the formula:

ATGAATGTATTAATCCTTTTATGTGATTATCATATACTACTGAATCA
TTATCAATCATATTTGCACTATTATTATCAGGG
GAATCAGTATATCAGGGCATGGGAACATTTATGGGTGGGAATCATTA
CTCAGGGGTGGGTCAGTTAATCCGTTGTGGGTG
GGTTTAGCTCCAGGCTACCTTAAGTAGCCTTTTTTTGTATATATGGA
TGTAGATTTCATTTGATCCTTAACTAATCTTGT
TTTCTTTCCCTTTCTTTCTGCTTTCTCTGCTTACTAACAACAACATT
CTACCTCAACACAAAACTACCTCAACTTAACTA
CCTCATTTGATTGCTCCTTGATTGTCTTTTTAGGGAGCATACTACTA.

4. A vector as claimed in claim 1, wherein said nucleotide molecule coding for said precursor is defined by the formula:

ACA CTG AGA
AAT GTC TAT GAC ATG AAA ATT GAG TGC CCC CAT ACA GTA AGT TTT GGG GAA AAC AGT GTG
ATA GGT TAT GTA GAA TTA CCC CCC GTG CCA TTG GCC GAC ACA GCA CAG ATG GTG CCT GAG
AGT TCT TGT AAC ATG GAT AAT CAC CAA TCG TTG AAT ACA ATA ACA AAA TAT ACC CAG GTA
AGT TGG AGA GGA AAG GCT GAT CAG TCA CAG TCT AGT CAA AAT TCA TTT GAG ACA GTG TCC
ACT GAA GTT GAC TTG AAA GGA ACA TGT GTT CTA AAA CAC AAA ATG GTG GAA GAA TCA TAC
CGT AGT AGG AAA TCA GTA ACC TGT TAC GAC CTG TCT TGC AAT AGC ACT TAC TGC AAG CCA
ACA CTA TAC ATG ATT GTA CCA ATT CAT GCA TGC AAT ATG ATG AAA AGC TGT TTG ATT GCA
TTG GGA CCA TAC AGA GTA CAG GTG GTT TAT GAG AGA AGT TAC TGT ATG ACA GGA GTC CTG
ATT GAA GGG AAA TGC TTT GTC CCA GAT CAA AGT GTG GTC AGT ATT ATC AAG CAT GGG ATC
TTT GAT ATT GCA AGT GTT CAT ATT GTA TGT TTC TTT GTT GCA GTT AAA GGG AAT ACT TAA

-continued

```
AAA ATT TTT GAA CAG GTT AAG AAA TCC TTT GAA TCA ACA TGC AAT GAT ACA GAG AAT AAA
GTG CAA GGA TAT TAT ATT TGT ATT GTA GGG GGA AAC TCT GCA CCA ATA TAT GTT CCA ACA
CTT GAT GAT TTC AGA TCC ATG GAA GCA TTT ACA GGA ATC TTC AGA TCA CCA CAT GGG GAA
GAT CAT GAT CTG GCT GGA GAA GAA ATT GCA TCT TAT TCT ATA GTC GGA CCT GCC AAT GCA
AAA GTT CCT CAT AGT GCT AGC TCA GAT ACA TTG AGC TTG ATT GCC TAT TCA GGT ATA CCA
TCT TAT TCT TCC CTT AGC ATC CTA ACA AGT TCA ACA GAA GCT AAG CAT GTA TTC AGC CCT
GGG TTG TTC CCA AAA CTT AAT CAC ACA AAT TGT GAT AAA AGT GCC ATA CCA CTC ATA TGG
ACT GGG ATG ATT GAT TTA CCT GGA TAC TAC GAA GCT GTC CAC CCT TGT ACA GTT TTT TGC
GTA TTA TCA GGT CCT GGG GCA TCA TGT GAA GCC TTT TCT GAA GGC GGG ATT TTC AAC ATA
ACC TCT CCC ATG TGC TTA GTG TCA AAA CAA AAT CGA TTC CGG TTA ACA GAACAG CAG GTG
AAT TTT GTG TGT CAG CGA GTG GAC ATG GAC ATT GTT GTG TAC TGC AAC GGG CAG AGG AAA
GTA ATA TTA ACA AAA ACT CTA GTT ATT GGA CAG TGT ATA TAT ACT ATA ACA AGC TTA TTG
TCA TTA CTA CCT GGA GTA GCA CAT TCT ATT GCT GTT GAA TTG TGT GTA CCT GGG TTC CAT
GGT TGG GCC ACA GCT GCT CTG CTT GTT ACA TTC TGT TTC GGA TGG GTT CTT ATA CGA GCA
ATT ACA TTT ATC ATA CTA ACA GTC CTA AAG TTC ATT GCT AAT ATT TTT CAC ACA AGT AAT
CAA GAG AAT AGG CTA AAA TCA GTA CTT AGA AAG ATA AAG GAA GAG TTT GAA GAA ACA AAA
GGC TCA ATG GTA TGT GAT GTC TGC AAG TAT GAG TGT GAA ACT TAT AAA GAA TTA AAG GCA
CAC GGG GTA TCA TGC CCC CAA TCT CAA TGT CCT TAC TGT TTT ACT CAT TGT GAA CCT ACA
GAA GCA GCA TTC CAA GCT CAT TAC AAG GTA TGC CAA GTT ACT CAC AGA TTC AGG GAT GAT
CTA AAG AAA ACT GTT ACT CCT CAA AAT TTT ACA CCA GGA TGT TAC CGG ACA CTA AAT TTA
TTT AGA TAC AAA AGC AGG TGC TAC ATC TTT ACA ATG TGG ATA TTT CTT CTT GTC TTA GAA
TCC ATA CTG TGG GCT GCA AGT GCA TCA GAG ACA CCA TTA ACT CCT GTC TGG AAT GAC AAT
GCC CAT GGG GTA GGT TCT GTT CCT ATG CAT ACA GAT TTA GAG CTT GAT TTC TCT TTA ACA
TCC AGT TCC AAG TAT ACA TAC CGT AGG AAG TTA ACA AAC CCA CTT GAG GAA GCA CAA TCC
ATT GAC CTA CAT ATT GAA ATA GAA GAA CAG ACA ATT GGT GTT GAT GTG CAT GCT CTA GGA
CAC TGG TTT GAT GGT CGT CTT AAC CTT AAA ACA TCC TTT CAC TGT TAT GGT GCT TGT ACA
AAG TAT GAA TAC CCT TGG CAT ACT GCA AAG TGC CAT TAT GAA AGA GAT TAC CAA TAT GAG
ACG AGC TGG GGT TGT AAT CCA TCA GAT TGT CCT GGG GTG GGC ACA GGC TGT ACA GCA TGT
GGT TTA TAC CTA GAT CAA CTG AAA CCA GTT GGT AGT GCT TAT AAA ATT ATC ACA ATA AGG
TAC AGC AGG AGA GTC TGT GTT CAG TTT GGG GAG GAA AAC CTT TGT AAG ATA ATA GAC ATG
AAT GAT TGT TTT GTA TCT AGG CAT GTT AAG GTC TGC ATA ATT GGT ACA GTA TCT AAA TTC
TCT CAG GGT GAT ACC TTA TTG TTT TTT GGA CCG CTT GAA GGT GGT GGT CTA ATA TTT AAA
CAC TGG TGT ACA TCC ACA TGT CAA TTT GGT GAC CCA GGA GAT ATC ATG AGT CCA AGA GAC
AAA GGT TTT TTA TGC CCT GAG TTT CCA GGT AGT TTC AGG AAG AAA TGC AAC TTT GCT ACT
ACC CCT ATT TGT GAG TAT GAT GGA AAT ATG GTC TCA GGT TAC AAG AAA GTG ATG GCG ACA
ATT GAT TCC TTC CAA TCT TTT AAT ACA AGC ACT ATG CAC TTC ACT GAT GAA AGG ATA GAG
TGG AAA GAC CCT GAT GGA ATG CTA AGG GAC CAT ATA AAC ATT TTA GTA ACG AAG GAC ATT
GAC TTT GAT AAC CTT GGT GAA AAT CCT TGC AAA ATT GGC TTA CAA ACA TCT TCT ATT GAG
GGG GCC TGG GGT TCT GGT GTG GGG TTC ACA TTA ACA TGT CTG GTA TCA CTA ACA GAA TGT
CCT ACC TTT TTG ACC TCA ATA AAG GCT TGT GAT AAG GCT ATC TGT TAT GGT GCA GAG AGT
GTA ACA TTG ACA AGA GGA CAA AAT ACA GTC AAG GTA TCA GGG AAA GGT GGC CAT AGT GGT
TCA ACA TTT AGG TGT TGC CAT GGG GAG GAC TGT TCA CAA ATT GGA CTC CAT GCT GCT GCA
```

-continued

CCT CAC CTT GAC AAG GTA AAT GGG ATT TCT GAG ATA GAA AAT AGT AAA GTA TAT GAT GAT
GGG GCA CCG CAA TGT GGG ATA AAA TGT TGG TTT GTT AAA TCA GGG GAA TGG ATT TCA GGG
ATA TTC AGT GGT AAT TGG ATT GTA CTC ATT GTC CTC TGT GTA TTT CTA TTG TTC TCC TTG
GTT TTA CTA AGC ATT CTC TGT CCC GTA AGG AAG CAT AAA AAA TCA TAG

5. A vector as claimed in claim 4, wherein said nucleotide molecule coding for said precursor further comprises at least one of (a) a leader-sequence that precedes said nucleotide molecule coding for said precursor, wherein said leader-sequence is comprised of a sequence defined by the formula:

CTAAATTCTGTGACTATCCTGTTCTTATGTATAGCTT-TAACATATATACTA-ATTTTTATATTCCAGTATACTCTATCTAACACAC-TAAAAAAAATAGTAGCTT-TCTAACCACAAAACTTAGATTCTTCTTCTGTAT-GATGTCTTAACATCTTGCG-GTGTCTACTACTA.

TAGTAGTAGACACCGCAAAAGAAAGCAGTCAATCAGCAAC-ATG GGG ATA TGG AAG TGG CTA GTG ATG GCC AGT TTA GTA TGG CCT GTT TTG, and (b) a tail-sequence that follows said nucleotide molecule coding for said precursor, wherein said tail-sequence is comprised of a sequence defined by the formula:

6. A vector as claimed in claim 1, wherein said nucleocapsid N protein has an amino acid sequence defined by the formula:

MET ALA THR MET GLU GLU LEU GLN ARG GLU ILE

ASN ALA HIS GLU GLY GLN LEU VAL ILE ALA ARG GLN LYS VAL ARG ASP ALA GLU LYS GLN

TYR GLU LYS ASP PRO ASP GLU LEU ASN LYS ARG THR LEU THR ASP ARG GLU GLY VAL ALA

VAL SER ILE GLN ALA LYS ILE ASP GLU LEU LYS ARG GLN LEU ALA ASP ARG ILE ALA THR

GLY LYS ASN LEU GLY LYS GLU GLN ASP PRO THR GLY VAL GLU PRO GLY ASP HIS LEU LYS

GLU ARG SER MET LEU SER TYR GLY ASN VAL LEU ASP LEU ASN HIS LEU ASP ILE ASP GLU

PRO THR GLY GLN THR ALA ASP TRP LEU SER ILE ILE VAL TYR LEU THR SER PHE VAL VAL

PRO ILE LEU LEU LYS ALA LEU TYR MET LEU THR THR ARG GLY ARG GLN THR THR LYS ASP

ASN LYS GLY THR ARG ILE ARG PHE LYS ASP ASP SER SER PHE GLU ASP VAL ASN GLY ILE

ARG LYS PRO LYS HIS LEU TYR VAL SER LEU PRO ASN ALA GLN SER SER MET LYS ALA GLU

GLU ILE THR PRO GLY ARG TYR ARG THR ALA VAL CYS GLY LEU TYR PRO ALA GLN ILE LYS

ALA ARG GLN MET ILE SER PRO VAL MET SER VAL ILE GLY PHE LEU ALA LEU ALA LYS ASP

TRP SER ASP ARG ILE GLU GLN TRP LEU ILE GLU PRO CYS LYS LEU LEU PRO ASP THR ALA

ALA VAL SER LEU LEU GLY GLY PRO ALA THR ASN ARG ASP TYR LEU ARG GLN ARG GLN VAL

ALA LEU GLY ASN MET GLU THR LYS GLU SER LYS ALA ILE ARG GLN HIS ALA GLU ALA ALA

GLY CYS SER MET ILE GLU ASP ILE GLU SER PRO SER SER ILE TRP VAL PHE ALA GLY ALA

PRO ASP ARG CYS PRO PRO THR CYS LEU PHE ILE ALA GLY ILE ALA GLU LEU GLY ALA PHE

PHE SER ILE LEU GLN ASP MET ARG ASN THR ILE MET ALA SER LYS THR VAL GLY THR SER

GLU GLU LYS LEU ARG LYS LYS SER SER PHE TYR GLN SER TYR LEU ARG ARG THR GLN SER

MET GLY ILE GLN LEU GLY GLN ARG ILE ILE VAL LEU PHE MET VAL ALA TRP GLY LYS GLU

ALA VAL ASP ASN PHE HIS LEU GLY ASP ASP MET ASP PRO GLU LEU ARG THR LEU ALA GLN

SER LEU ILE ASP VAL LYS VAL LYS GLU ILE SER ASN GLN GLU PRO LEU LYS LEU.

7. A vector as claimed in claim 1, wherein said precursor has an amino acid sequence defined by the formula:

THR LEU ARG

-continued

```
ASN VAL TYR ASP MET LYS ILE GLU CYS PRO HIS THR VAL SER PHE GLY GLU ASN SER VAL
ILE GLY TYR VAL GLU LEU PRO PRO VAL PRO LEU ALA ASP THR ALA GLN MET VAL PRO GLU
SER SER CYS ASN MET ASP ASN HIS GLN SER LEU ASN THR ILE THR LYS TYR THR GLN VAL
SER TRP ARG GLY LYS ALA ASP GLN SER GLN SER SER GLN ASN SER PHE GLU THR VAL SER
THR GLU VAL ASP LEU LYS GLY THR CYS VAL LEU LYS HIS LYS MET VAL GLU GLU SER TYR
ARG SER ARG LYS SER VAL THR CYS TYR ASP LEU SER CYS ASN SER THR TYR CYS LYS PRO
THR LEU TYR MET ILE VAL PRO ILE HIS ALA CYS ASN MET MET LYS SER CYS LEU ILE ALA
LEU GLY PRO TYR ARG VAL GLN VAL VAL TYR GLU ARG SER TYR CYS MET THR GLY VAL LEU
ILE GLU GLY LYS CYS PHE VAL PRO ASP GLN SER VAL VAL SER ILE ILE LYS HIS GLY ILE
PHE ASP ILE ALA SER VAL HIS ILE VAL CYS PHE PHE VAL ALA VAL LYS GLY ASN THR TYR
LYS ILE PHE GLU GLN VAL LYS LYS SER PHE GLU SER THR CYS ASN ASP THR GLS ASN LYS
VAL GLN GLY TYR TYR ILE CYS ILE VAL GLY GLY ASN SER ALA PRO ILE TYR VAL PRO THR
LEU ASP ASP PHE ARG SER MET GLU ALA PHE THR GLY ILE PHE ARG SER PRO HIS GLY GLU
ASP HIS ASP LEU ALA GLY GLU GLU ILE ALA SER TYR SER ILE VAL GLY PRO ALA ASN ALA
LYS VAL PRO HIS SER ALA SER SER ASP THR LEU SER LEU ILE ALA TYR SER GLY ILE PRO
SER TYR SER SER LEU SER ILE LEU THR SER SER THR GLU ALA LYS HIS VAL PHE SER PRO
GLY LEU PHE PRO LYS LEU ASN HIS THR ASN CYS ASP LYS SER ALA ILE PRO LEU ILE TRP
THR GLY MET ILE ASP LEU PRO GLY TYR TYR GLU ALA VAL HIS PRO CYS THR VAL PHE CYS
VAL LEU SER GLY PRO GLY ALA SER CYS GLU ALA PHE SER GLU GLY GLY ILE PHE ASN ILE
THR SER PRO MET CYS LEU VAL SER LYS GLN ASN ARG PHE ARG LEU THR GLU GLN GLN VAL
ASN PHE VAL CYS GLN ARG VAL ASP MET ASP ILE VAL VAL TYR CYS ASN GLY GLN ARG LYS
VAL ILE LEU THR LYS THR LEU VAL ILE GLY GLN CYS ILE TYR THR ILE THR SER LEU PHE
SER LEU LEU PRO GLY VAL ALA HIS SER ILE ALA VAL GLU LEU CYS VAL PRO GLY PHE HIS
GLY TRP ALA THR ALA ALA LEU LEU VAL THR PHE CYS PHE GLY TRP VAL LEU ILE PRO ALA
ILE THR PHE ILE ILE LEU THR VAL LEU LYS PHE ILE ALA ASN ILE PHE HIS THR SER ASN
GLN GLU ASN ARG LEU LYS SER VAL LEU ARG LYS ILE LYS GLU GLU PHE GLU LYS THR LYS
GLY SER MET VAL CYS ASP VAL CYS LYS TYR GLU CYS GLU THR TYR LYS GLU LEU LYS ALA
HIS GLY VAL SER CYS PRO GLN SER GLN CYS PRO TYR CYS PHE THR HIS CYS GLU PRO THR
GLU ALA ALA PHE GLN ALA HIS TYR LYS VAL CYS GLN VAL THR HIS ARG PHE ARG ASP ASP
LEU LYS LYS THR VAL THR PRO GLN ASN PHE THR PRO GLY CYS TYR ARG THR LEU ASN LEU
PHE ARG TYR LYS SER ARG CYS TYR ILE PHE THR MET TRP ILE PHE LEU LEU VAL LEU GLU
SER ILE LEU TRP ALA ALA SER ALA SER GLU THR PRO LEU THR PRO VAL TRP ASN ASP ASN
ALA HIS GLY VAL GLY SER VAL PRO MET HIS THR ASP LEU GLU LEU ASP PHE SER LEU THR
SER SER SER LYS TYR THR TYR ARG ARG LYS LEU THR ASN PRO LEU GLU GLU ALA GLN SER
ILE ASP LEU HIS ILE GLU ILE GLU GLU GLN THR ILE GLY VAL ASP VAL HIS ALA LEU GLY
HIS TRP PHE ASP GLY ARG LEU ASN LEU LYS THR SER PHE HIS CYS TYR GLY ALA CYS THR
LYS TYR GLU TYR PRO TRP HIS THR ALA LYS CYS HIS TYR GLU ARG ASP TYR GLN TYR GLU
THR SER TRP GLY CYS ASN PRO SER ASP CYS PRO GLY VAL GLY THR GLY CYS THR ALA CYS
GLY LEU TYR LEU ASP GLN LEU LYS PRO VAL GLY SER ALA TYR LYS ILE ILE THR ILE ARG
TYR SER ARG ARG VAL CYS VAL GLN PHE GLY GLU GLU ASN LEU CYS LYS ILE ILE ASP MET
ASN ASP CYS PHE VAL SER ARG HIS VAL LYS VAL CYS ILE ILE GLY THR VAL SER LYS PHE
SER GLN GLY ASP THR LEU LEU PHE PHE GLY PRO LEU GLU GLY GLY GLY LEU ILE PHE LYS
```

-continued

```
HIS TRP CYS THR SER THR CYS GLN PHE GLY ASP PRO GLY ASP ILE MET SER PRO ARG ASP
LYS GLY PHE LEU CYS PRO GLU PHE PRO GLY SER PHE ARG LYS LYS CYS ASN PHE ALA THR
THR PRO ILE CYS GLU TYR ASP GLY ASN MET VAL SER GLY TYR LYS LYS VAL MET ALA THR
ILE ASP SER PHE GLN SER PHE ASN THR SER THR MET HIS PHE THR ASP GLU ARG ILE GLU
TRP LYS ASP PRO ASP GLY MET LEU ARG ASP HIS ILE ASN ILE LEU VAL THR LYS ASP ILE
ASP PHE ASP ASN LEU GLY GLU ASN PRO CYS LYS ILE GLY LEU GLN THR SER SER ILE GLU
GLY ALA TRP GLY SER GLY VAL GLY PHE THR LEU THR CYS LEU VAL SER LEU THR GLU CYS
PRO THR PHE LEU THR SER ILE LYS ALA CYS ASP LYS ALA ILE CYS TYR GLY ALA GLU SER
VAL THR LEU THR ARG GLY GLN ASN THR VAL LYS VAL SER GLY LYS GLY GLY HIS SER GLY
SER THR PHE ARG CYS CYS HIS GLY GLU ASP CYS SER GLN ILE GLY LEU HIS ALA ALA ALA
PRO HIS LEU ASP LYS VAL ASN GLY ILE SER GLU ILE GLU ASN SER LYS VAL TYR ASP ASP
GLY ALA PRO GLN CYS GLY ILE LYS CYS TRP PHE VAL LYS SER GLY GLU TRP ILE SER GLY
ILE PHE SER GLY ASN TRP ILE VAL LEU ILE VAL LEU CYS VAL PHE LEU LEU PHE SER LEU
VAL LEU LEU SER ILE LEU CYS PRO VAL ARG LYS HIS LYS LYS SER.
```

8. A vector as claimed in claim 7, wherein said amino acid sequence is preceded by a leader-sequence that comprises a sequence defined by the formula:

```
MET GLY ILE TRP LYS TRP LEU VAL MET ALA SER LEU VAL
TRP PRO VAL LEU
```

9. A cDNA molecule comprising a nucleotide molecule selected from the group consisting of a nucleotide molecule coding for a Hantaan virus nucleocapsid N protein and a nucleotide molecule coding for a precursor of Hantaan virus G1 and G1 glycoproteins.

10. A cDNA molecule as claimed in claim 9, wherein said nucleotide molecule coding for said nucleocapsid N protein is defined by the formula:

```
                                                ATG GCA ACT ATG GAG GAA TTA CAG AGG GAA ATC
AAT GCC CAT GAG GGT CAA TTA GTG ATA GCC AGG CAG AAG GTG AGG GAT GCA GAA AAA CAG
TAT GAA AAG GAT CCA GAT GAG TTG AAC AAG AGA ACA TTA ACT GAC CGA GAG GGC GTT GCA
GTA TCT ATC CAG GCA AAA ATT GAT GAG TTA AAA AGG CAA CTG GCA GAT AGG ATT GCA ACT
GGG AAA AAC CTT GGG AAG GAA CAA GAT CCA ACA GGG GTG GAG CCT GGA GAC CAT CTG AAA
GAG AGG TCA ATG CTC AGT TAT GGT AAT GTG CTG GAT TTA AAC CAT TTG GAT ATT GAT GAA
CCT ACA GGA CAG ACA GCA GAC TGG CTG AGC ATC ATC GTC TAT CTT ACA TCC TTT GTC GTC
CCG ATA CTT CTG AAA GCT CTG TAT ATG TTG ACA ACA AGG GGG AGG CAA ACT ACC AAG GAT
AAT AAA GGG ACC CGG ATT CGA TTT AAG GAT GAT AGC TCG TTC GAG GAT GTT AAC GGT ATC
CGG AAA CCA AAA CAT CTT TAC GTG TCC TTG CCA AAT GCA CAG TCA GCA TGA AGG CA GAA
GAG ATT ACA CCT GGT AGA TAT AGA ACA GCA GTC TGT GGG CTC TAC CCT GCA CAG ATT AAG
GCA CGG CAG ATG ATC AGT CCA GTT ATG AGT GTA ATT GGT TTT CTA GCA TTA GCA AGG ACT GAC CGT ACT TGG
TGG AGT GAT CGT ATC GAA CAA TGG TTA ATT GAA CCT GCT AAG CTT CTT CCA GAT ACA GCA
GCA GTT AGC CTC CTT GGT GGT CCT GCA ACA AAC AGG GAC TAC TTA CGG CAG CGG CAA GTG
GCA TTA GGC AAT ATG GAG ACA AAG GAG TCA AAG GCT ATA CGC CAG CAT GCA GAA GCA GCT
GGC TGT AGC ATG ATT GAA GAT ATT GAG TCA CCA TCA TCA ATA TGG GTT TTT GCT GGA GCA
CCA GAC CGT TGT CCA CCA ACA TGT TTG TTT ATA GCA GGT ATT GCT GAG CTT GGG GCA TTT
TTT TCC ATC CTG CAG GAC ATG CGA AAT ACA ATC ATG GCA TCT AAG ACA GTT GGA ACA TCT
GAG GAG AAG CTA CGG AAG AAA TCA TCA TTT TAT CAG TCC TAC CTC AGA AGG ACA CAA TCA
ATG GGG ATA CAA CTA GGC CAG AGA ATT ATT GTG CTC TTC ATG GTT GCC TGG GGA AAG GAG
```

GCT TGT GAC AAC TTC CAC TTA GGG GAT GAT ATG GAT CCT GAG CTA AGG ACA CTG GCA CAG

AGC TTG ATT GAT GTC AAA GTG AAG GAA ATC TCC AAC CAA GAG CCT TTG AAA CTC TAA.

11. A cDNA molecule as claimed in claim 10, wherein said nucleotide molecule coding for said nucleocapsid N protein further comprises at least one of
(a) a leader-sequence that precedes said nucleotide molecule coding for said nucleocapsid N protein, wherein said leader-sequence is comprised of a sequence defined by the formula:

TAGTAGTAGACTCCCTAAAGAGCTAC-
TAGAACAACG, and (b) a tail-sequence that follows said nucleotide molecule coding for said nucleocapsid N protein, wherein sad tail-sequence is comprised of a sequence defined by the formula:

ATGAATGTATTAATCCTTTTATGTGATTATCATATACTACTGAATCATTA

TCAATCATATTTGCACTATTATTATCAGGG

GAATCAGTATATCAGGGCATGGGAACATTTATGGGTGGGAATCATTACTC

AGGGGTGGGTCAGTTAATCCGTTGTGGGTG

GGTTTAGCTCCAGGCTACCTTAAGTAGCCTTTTTTTGTATATATGGATGT

AGATTTCATTTGATCCTTAACTAATCTTGT

TTTCTTTCCCTTTCTTTCTGCTTTCTCTGCTTACTAACAACAACATTCTA

CCTCAACACAAAACTACCTCAACTTAACTA

CCTCATTTGATTGCTCCTTGATTGTCTTTTTAGGGAGCATACTACTA.

12. A cDNA molecule as claimed in claim 9, wherein said nucleotide molecule coding for said precursor is defined by the formula:

ACA CTG AGA

AAT GTC TAT GAC ATG AAA ATT GAG TGC CCC CAT ACA GTA AGT TTT GGG GAA AAC AGT GTG

ATA GGT TAT GTA GAA TTA CCC CCC GTG CCA TTG GCC GAC ACA GCA CAG ATG GTG CCT GAG

AGT TCT TGT AAC ATG GAT AAT CAC CAA TCG TTG AAT ACA ATA ACA AAA TAT ACC CAA GTA

AGT TGG AGA GGA AAG GCT GAT CAG TCA CAG TCT AGT CAA AAT TCA TTT GAG ACA GTG TCC

ACT GAA GTT GAC TTG AAA GGA ACA TGT GTT CTA AAA CAC AAA ATG GTG GAA GAA TCA TAC

CGT AGT AGG AAA TCA GTA ACC TGT TAC GAC CTG TCT TGC AAT AGC ACT TAC TGC AAG CCA

ACA CTA TAC ATG ATT GTA CCA ATT CAT GCA TGC AAT ATG ATG AAA AGC TGT TTG ATT GCA

TTG GGA CCA TAC AGA GTA CAG GTG GTT TAT GAG AGA AGT TAC TGT ATG ACA GGA GTC CTG

ATT GAA GGG AAA TGC TTT GTC CCA GAT CAA AGT GTG GTC AGT ATT ATC AAG CAT GGG ATC

TTT GAT ATT GCA AGT GTT CAT ATT GTA TGT TTC TTT GTT GCA GTT AAA GGG AAT ACT TAT

AAA ATT TTT GAA CAG GTT AAG AAA TCC TTT GAA TCA ACA TGC AAT GAT ACA GAG AAT AAA

GTG CAA GGA TAT TAT ATT TGT ATT GTA GGG GGA AAC TCT GCA CCA ATA TAT GTT CCA ACA

CTT GAT GAT TTC AGA TCC ATG GAA GCA TTT ACA GGA ATC TTC AGA TCA CCA CAT GGG GAA

GAT CAT GAT CTG GCT GGA GAA GAA ATT GCA TCT TAC TCT ATA GTC GGA CCT GCC AAT GCA

AAA GTT CCT CAT AGT GCT AGC TCA GAT ACA TTG AGC TTG ATT GCC TAT TCA GGT ATA CCA

TCT TAT TCT TCC CTT AGC ATC CTA ACA AGT TCA ACA GAA GCT AAG CAT GTA TTC AGC CCT

GGG TTG TTC CCA AAA CTT AAT CAC ACA AAT TGT GAT AAA AGT GCC ATA CCA CTC ATA TGG

ACT GGG ATG ATT GAT TTA CCT GGA TAC TAC GAA GCT GTC CAC CCT TGT ACA GTT TTT TGC

GTA TTA TCA GGT CCT GGG GCA TCA TGT GAA GCC TTT TCT GAA GGC GGG ATT TTC AAC ATA

ACC TCT CCC ATG TGC TTA GTG TCA AAA CAA AAT CGA TTC CGG TTA ACA GAA CAG CAA GTG

AAT TTT GTG TGT CAG CGA GTG GAC ATG GAC ATT GTT GTG TAC TGC AAC GGG CAG AGG AAA

-continued

```
GTA ATA TTA ACA AAA ACT CTA GTT ATT GGA CAG TGT ATA TAT ACT ATA ACA AGC TTA TTC
TCA TTA CTA CCT GGA GTA GCA CAT TCT ATT GCT GTT GAA TTG TGT GTA CCT GCG TTC CAT
GGT TGG GCC ACA GCT GCT CTG CTT GTT ACA TTC TGT TTC GGA TGG GTT CTT ATA CCA GCA
ATT ACA TTT ATC ATA CTA ACA GTC CTA AAG TTC ATT GCT AAT ATT TTT CAC ACA AGT AAT
CAA GAG AAT AGG CTA AAA TCA GTA CTT AGA AAG ATA AAG GAA GAG TTT GAA AAA ACA AAA
GGC TCA ATG GTA TGT GAT GTC TGC AAG TAT GAG TGT GAA ACG TAT AAA GAA TTA AAG CA
CAC GGG GTA TCA TGC CCC CAA TCT CAA TGT CCT TAC TGT TTT ACT CAT TGT GAA CCA ACA
GAA GCA GCA TTC CAA GCT CAT TAC AAG GTA TGG CAA GTT ACT CAC AGA TTC AGG GAT GAT
CTA AAG AAA ACT GTT ACT CCT CAA AAT TTT ACA CCA GGA TGT TAC CGG ACA CTA AAT TTA
TTT AGA TAC AAA AGC AGG TGC TAC ATC TTT ACA ATG TGG ATA TTT CTT CTT GTC TTA GAA
TCC ATA CTG TGG GCT GCA AGT GCA TCA GAG ACA CCA TTA ACT CCT GTC TGG AAT GAC AAT
GCC CAT GGG GTA GGT TCT GTT CCT ATG CAT ACA GAT TTA GAG CTT GAT TTC TCT TTA ACA
TCC AGT TCC AAG TAT ACA TAC CGT AGG AAG TTA ACA AAC CCA CTT GAG GAA GCA CAA TCC
ATT GAC CTA CAT ATT GAA ATA GAA GAA CAG ACA ATT GGT GTT GAT GTG CAT GCT CTA GGA
CAC TGG TTT GAT GGT CGT CTT AAC CTT AAA ACA TCC TTT CAC TGT TAT GGT GCT TGT ACA
AAG TAT GAA TAC CCT TGG CAT ACT GCA AAG TGC CAT TAT GAA AGA GAT TAC CAA TAT GAG
ACG AGC TGG GGT TGT AAT CCA TCA GAT TGT CCT GGG GTG GGC ACA GGC TGT ACA GCA TGT
GGT TTA CTA GAT CAA CTG AAA CCA GTT GGT AGT GCT TAT AAA ATT ATC ACA ATA AGG
TAC AGC AGG AGA GTC TGT GTT CAG TTT GGG GAG GAA AAC CTT TGT AAG ATA ATA GAC ATG
AAT GAT TGT TTT GTA TCT AGG CAT GTT AAG GTC TGC ATA ATT GGT ACA GTA TCT AAA TTC
TCT CAG GGT GAT ACC TTA TTG TTT TTT GGA CCG CTT GAA GGT GGT GGT CTA ATA TTT AAA
CAC TGG TGT ACA TCC ACA TGT CAA TTT GGT GAC CCA GGA GAT ATC ATG AGT CCA AGA GAC
AAA GGT TTT TTA TGC CCT GAG TTT CCA GGT AGT TTC AGG AAG AAA TGC AAC TTT GCT ACT
ACC CCT ATT TGT GAG TAT GAT GGA AAT ATG GTC TCA GGT TAC AAG AAA GTG ATG GCG ACA
ATT GAT TCC TTC CAA TCT TTT AAT ACA AGC ACT ATG CAC TTC ACT GAT GAA AGG ATA GAG
TGG AAA GAC CCT GAT GGA ATG CTA AGG GAC CAT ATA AAC ATT TTA GTA ACG AAG GAC ATT
GAC TTT GAT AAC CTT GGT GAA AAT CCT GCA AAA ATT GGC CTA CAA ACA TCT TCT ATT GAG
GGG GCC TGG GGT TCT GGT GTG GGG TTC ACA TTA ACA TGT CTG GTA TCA CTA ACA GAA TGT
CCT ACC TTT TTG ACC TCA ATA AAG GCT TGT GAT AAG GCT ATC TGT TAT GGT GCA GAG AGT
GTA ACA TTG ACA AGA GGA CAA AAT ACA GTC AAG GTA TCA GGG AAA GGT GGC CAT AGT GGT
TCA ACA TTT AGG TGT TGC CAT GGG GAG GAC TGT TCA CAA ATT GGA CTC CAT GCT GCT GCA
CCT CAC CTT GAC AAG GTA AAT GGG ATT TCT GAG ATA GAA AAT AGT AAA GTA TAT GAT GAT
GGG GCA CCG CAA TGT GGG ATA AAA TGT TGG TTT GTT AAA TCA GGG AAA TGG ATT CA GGG
ATA TTC AGT GGT AAT TGG ATT GTA CTC ATT GTC CTC TGT GTA TTT CTA TTG TTC TCC TTG
GTT TTA CTA AGC ATT CTC TGT CCC GTA AGG AAG CAT AAA AAA TCA TAG.
```

13. A cDNA molecule as claimed in claim 12, wherein said nucleotide molecule coding for said precursor further comprises at least one of
   (a) a leader-sequence that precedes said nucleotide molecule coding for said precursor, wherein said leader-sequence is comprised of a sequence defined by the formula:

TAGTAGTAGACACCGCAAAAGAAAGCAGTCAATCAGCAAC—
   ATG GGG ATA TGG AAG TGG CTA GTG ATG GCC AGT TTA GTA
   TGG CCT GTT TTG, and (b) a tail-sequence that follows said nucleotide molecule coding for said precursor, wherein said tail-sequence is comprised of a sequence defined by the formula:

CTAAATTCTGTGACTATCCTGTTCTTATGTATAGCTTTAACATATATACTA—
ATTTTTATATTCCAGTATACTCTATCTAACACACTAAAAAAAATAGTAGCTT—
TCTAACCACAAAACTTAGATTCTTCTTCTGTATGATGTCTTAACATCTTGCG—
GTGTCTACTACTA.

* * * * *